United States Patent
Yamaguchi et al.

(10) Patent No.: US 9,329,117 B2
(45) Date of Patent: May 3, 2016

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventors: Mitsushiro Yamaguchi, Hachioji (JP); Tetsuya Tanabe, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 153 days.

(21) Appl. No.: 14/266,869

(22) Filed: May 1, 2014

(65) Prior Publication Data
US 2014/0231619 A1 Aug. 21, 2014

Related U.S. Application Data

(63) Continuation of application No. PCT/JP2012/077986, filed on Oct. 30, 2012.

(30) Foreign Application Priority Data

Nov. 10, 2011 (JP) .................................. 2011-246345

(51) Int. Cl.
*G01N 15/14* (2006.01)
*G01N 21/64* (2006.01)
*G02B 21/00* (2006.01)

(52) U.S. Cl.
CPC ............ *G01N 15/14* (2013.01); *G01N 15/1429* (2013.01); *G01N 21/6408* (2013.01);
(Continued)

(58) Field of Classification Search
CPC .............. G01N 15/14; G01N 15/1429; G01N 21/6408; G01N 21/6452; G01N 21/6458; G01N 2015/149; G01N 2021/6419; G01N 2021/6421; G02B 21/00
USPC ........................................ 250/206.1; 436/164
See application file for complete search history.

(56) References Cited

U.S. PATENT DOCUMENTS

| 3,887,812 A | 6/1975 | Hirschfeld |
| 4,251,733 A | 2/1981 | Hirleman, Jr. |

(Continued)

FOREIGN PATENT DOCUMENTS

| EP | 1906172 A1 | 4/2008 |
| EP | 1 970 694 A1 | 9/2008 |

(Continued)

OTHER PUBLICATIONS

Extended European Search Report dated Oct. 20, 2014, issued in related EP Application No. 12770835.2 (10 pages).

(Continued)

*Primary Examiner* — Renee D Chavez
(74) *Attorney, Agent, or Firm* — Westerman, Hattori, Daniels & Adrian, LLP

(57) ABSTRACT

There is provided a way of enabling the discrimination or identification of the kind of a light-emitting particle corresponding to each pulse form signal in the scanning molecule counting method using the optical measurement by the confocal or multiphoton microscope. In the inventive technique, the position of a light detection region in a sample solution periodically along a predetermined route is moved in measuring the light intensity from the light detection region; and a signal of light from a light-emitting particle is detected individually. Then, an index value indicating a translational diffusional characteristic of one light-emitting particle in a plane perpendicular to the moving direction of the light detection region is determined based upon intensity values of signals of light of the same light-emitting particle for identifying a light-emitting particle.

12 Claims, 9 Drawing Sheets

Figure 2A:
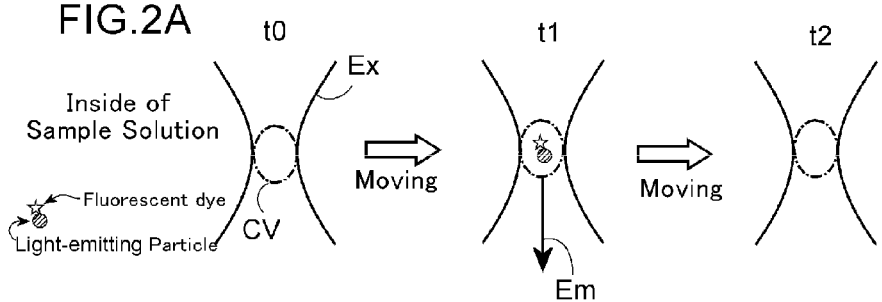

(52) U.S. Cl.
CPC ........ *G01N21/6452* (2013.01); *G01N 21/6458* (2013.01); *G02B 21/00* (2013.01); *G01N 2015/149* (2013.01); *G01N 2021/6419* (2013.01); *G01N 2021/6421* (2013.01)

(56) References Cited

U.S. PATENT DOCUMENTS

| | | | |
|---|---|---|---|
| 5,011,279 | A | 4/1991 | Auweter et al. |
| 5,866,336 | A | 2/1999 | Nazarenko et al. |
| 5,949,532 | A | 9/1999 | Schrof et al. |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 7,330,255 | B2 | 2/2008 | Cluzel et al. |
| 8,264,684 | B2 | 9/2012 | Livingston |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0051051 | A1 | 3/2004 | Kato et al. |
| 2004/0150880 | A1 | 8/2004 | Nakata et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2008/0052009 | A1 | 2/2008 | Chiu et al. |
| 2008/0117421 | A1 | 5/2008 | Yamaguchi et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2010/0301231 | A1 | 12/2010 | Yamaguchi |
| 2012/0319009 | A1 | 12/2012 | Yamaguchi et al. |
| 2013/0048875 | A1 | 2/2013 | Yamaguchi et al. |
| 2013/0228705 | A1 | 9/2013 | Nishikawa et al. |

FOREIGN PATENT DOCUMENTS

| | | |
|---|---|---|
| JP | 04-337446 A | 11/1992 |
| JP | 2002-507762 A | 3/2002 |
| JP | 2002-543414 A | 12/2002 |
| JP | 2004-506192 A | 2/2004 |
| JP | 2005-17282 A | 1/2005 |
| JP | 2005-098876 A | 4/2005 |
| JP | 2005-099662 A | 4/2005 |
| JP | 2005-164560 A1 | 6/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2011-002415 A | 1/2011 |
| JP | 2011-508219 A | 3/2011 |
| RU | 2 223 504 C1 | 2/2004 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 03/021231 A2 | 3/2003 |
| WO | 2006/084283 A2 | 8/2006 |
| WO | 2007010803 A1 | 1/2007 |
| WO | 2007/118209 A2 | 10/2007 |
| WO | 2007147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/050011 A1 | 4/2012 |
| WO | 2013/031309 A1 | 3/2013 |
| WO | 2013/031439 A1 | 3/2013 |

OTHER PUBLICATIONS

Extended European Search Report dated Apr. 24, 2015, issued in European Patent Application No. 11834195.7 (7 pages).
English Translation of Office Action dated Jul. 1, 2014, issued in related Chinese Patent Application No. 201180049568.7 (5 pages).
English Translation of Chinese Office Action dated Aug. 13, 2014, issued in related Chinese Application No. 201180050724.1 (15 pages).
Final Office Action dated Sep. 28, 2015, issued in U.S. Appl. No. 13/746,968 (24 pages).
Final Office Action dated Sep. 29, 2015, issued in U.S. Appl. No. 13/946,091 (23 pages).
Goodwin et al. "Rapid sizing of individual fluorescently stained DNA fragments by flow cytometry," Nucleic Acids Research, 1993, vol. 21, No. 4 pp. 803-806.
Keller et al. "Single-Molecule Fluorescence Analysis in Solution," Applied Spectroscopy, 1996, vol. 50, No. 7, pp. 12A-32A.
Lee et al. "Laser-Induced Fluorescence Detection of a Single Molecule in a Capillary," Analytical Chemistry, Dec. 1, 1994, vol. 66, No. 23, pp. 4142-4149.
Li et al. "Ultrasensitive Coincidence Fluorescence Detection of Single DNA Molecules," Analytical Chemistry, Apr. 1, 2003, vol. 75, No. 7, pp. 1664-1670.
Nie et al. "Probing Individual Molecules with Confocal Fluorescence Microscopy," Science, Nov. 11, 1994, vol. 266, pp. 1018-1021.
Tahari, "Fluorescence Correlation Spectroscopy: Ultrasensitive Detection in Clear and Turbid Media," University of Illinois, 2005, pp. 1-88.
Wu et al. "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, pp. 2157-2159.
Itoh et al. "A New Method for Detection of Influenza Viruses by Single Particle-Recognition Based on the Principle of Fluorescence Correlation Spectroscopy," Chemistry and Biology, 2009, vol. 47, No. 12, pp. 823-830.
Carlsson K et al: "Three-dimensional microscopy using a confocal laser scanning microscope", Optics Letters, Optical Society of America, vol. 10, No. 2, Feb. 1985 pp. 53-55, XP007922413.
Chinese Office Action dated Feb. 7, 2013, issued in related Chinese application No. 201180011644.5 with translation.
Extended European search report dated Mar. 28, 2013, issued in related EP application No. 11750481.1.
Japanese Office Action dated Dec. 18, 2012, issued in related Japanese application No. 2012-503060 with English translation.
International Search Report dated Mar. 29, 2011 issued in related PCT/JP2011/053481.
International Search Report dated Nov. 29, 2011, issued in PCT/JP2011/072898.
International Preliminary Report on Patentability issued in related PCT/JP2011/053481 with English translation.
Chinese Office Action dated Aug. 9, 2013, issued in related Chinese application No. 201180011640.7 with English translation.
International Search Report dated Mar. 29, 2011, issued in related PCT/JP2011/053482 with English translation.
International Preliminary Report on Patentability issued in related PCT/JP2011/053482 with English translation.
Supplemental European Search Report dated Jun. 17, 2013, issued in corresponding EP application No. 11832447.
US Office Action dated Jan. 3, 2014, issued in related U.S. Appl. No. 13/597,825.

(56) References Cited

OTHER PUBLICATIONS

Chinese Office Action dated Aug. 13, 2013, issued in related Chinese application No. 201180011655.3 with English translation.
International Search Report dated Mar. 29, 2011, issued in related PCT/JP2011/053483.
International Preliminary Report on Patentability issued in related PCT/JP2011/053483 with English translation.
Hebert, B et al. "Spatiotemporal Image Correlation Spectroscopy (STICS) Theory, Verification, and Application to Protein Velocity Mapping in Living CHO Cells", Biophysical Journal vol. 88, May 2005 pp. 3601-3614.
US Office Action dated Apr. 2, 2013, issued in related U.S. Appl. No. 13/596,280.
Park et al, "Counting the Number of Fluorophores Labeled in Biomolecules by Observing the Fluorescence-Intensity Transient of a Single Molecule", Bulletin of the Chemical Society of Japan, dated Aug. 30, 2005, vol. 78, No. 9, pp. 1612-1618.
US Office Action dated Oct. 4, 2013, issued in related U.S. Appl. No. 13/596,243.
US Office Action dated Sep. 16, 2013, issued in related U.S. Appl. No. 13/862,021.
International Search Report dated Nov. 29, 2011, issued in related PCT/JP2011/072939.
P. Kask et al., "Fluorescence-intensity Distribution Analysis and its Application in Biomolecular Detection Technology", PNAS, vol. 96, No. 24, pp. 13756-13761, (1999).
US Office Action dated Oct. 22, 2013, issued in related U.S. Appl. No. 13/864,867.
US Notice of Allowance dated Jun. 16, 2014, issued in related U.S. Appl. No. 13/864,867.
Kinjo, M. "Single Molecule Detection by Fluorescence Correlation Spectroscopy", Proteins, Nucleic Acids and Enzymes, 1999, vol. 44, No. 9, pp. 1431-1438.
Meyer-Almes, F.J. "A New Method for Use in Molecular Diagnostics and High Throughput Pharmaceutical Screening based on Fluorescence Correlation Spectroscopy", Nanoparticle Immunoassays, R. Ridger, edit., Springer, Berlin, 2000, pp. 204-224.
Kato, N. et al., "A Single Molecule Analyzer that Enables New Analysis of DNA and Protein Interactions", Gene Medicine, 2002, vol. 6, No. 2, pp. 271-277.
Kask, P. et al., "Two-Dimensional Fluorescence Intensity Distribution Analysis: Theory and Applications", Biophysical Journal, vol. 78, 2000, pp. 1703-1713.
Nagai, T. et al., "How to Measure Diffusion Coefficient of Biomolecules in Living Cells", Biophysics vol. 49, No. 4, 2009, pp. 181-186.
Kinjo, M. et al., "Analysis of DNA Structure by Measurement of Diffusion Rate", Japanese Society of Biorheology, vol. 9, No. 2, 1995, pp. 74-83.
Rigler R. et al., "Fluorescence Correlation Spectroscopy with High Count Rate and Low Background: Analysis of Translational Diffusion", European Biophysics Journal, 1993, pp. 169-175.
Machan, Radek et al., "Recent Developments in Fluorescence Correlation Spectroscopy for Diffusion Measurements in Planar Lipid Membranes", International Journal of Molecular Sciences, 2010, pp. 427-457, ISSN 1422-0067.
International Search Report dated Nov. 27, 2012, issued in related PCT/JP2012/077986.
Office Action dated Aug. 11, 2015, issued in Japanese application No. 2012-539662, with English translation (7 pages).
Zdenek Petrasek et al. "Precise Measurement of Diffusion Coefficients using Scanning Fluorescence Correlation Spectroscopy", Biophysical Journal, Feb. 2008, vol. 94, pp. 1437-1448.
Kaupo Palo et al. "Fluorescence Intensity Multiple Distributions Analysis: Concurrent Determination of Diffusion Times and Molecular Brightness", Biophysical Journal, Dec. 2000, pp. 2858-2866, vol. 79, Cell Press, US.
Chrisitan Tischer et al. "Determination and Correction of Position Detection Nonlinearity in Single Particle Tracking and Three-Dimensional Scanning Probe Microscopy", Microscopy and Microanalysis, Springer, 2004, pp. 425-434, vol. 10, New York, US.
Extended European Search Report dated Oct. 29, 2015, issued in counterpart EP Patent Application No. 12848150.4, (12 pages).
Riegler R. et al., "Fluorescence correlations, single molecule detection and large number screening Applications in biotechnology", Journal of Biotechnology, Elsevier Science Publishers, Amsterdam, NL, Jul. 31, 1995, vol. 41, No. 2, pp. 177-186.

FIG.1A
FIG.1B
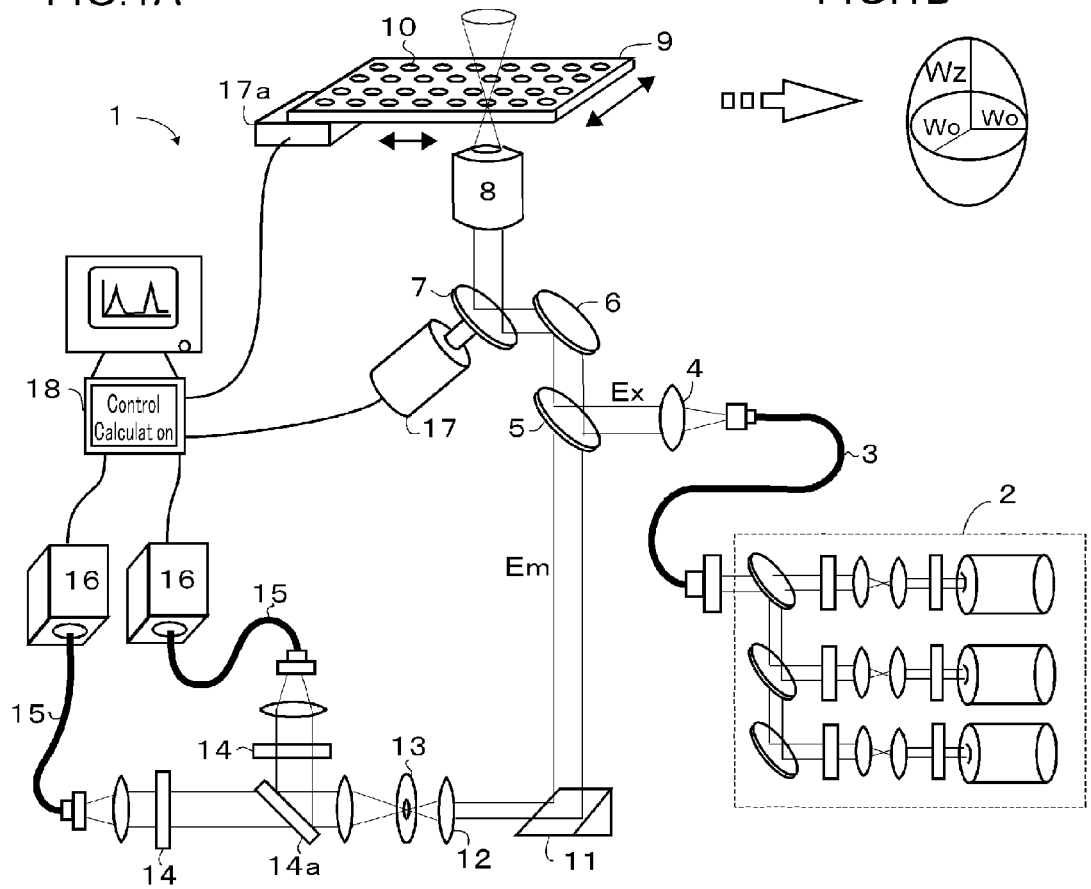
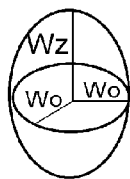
FIG.1C
FIG.1D
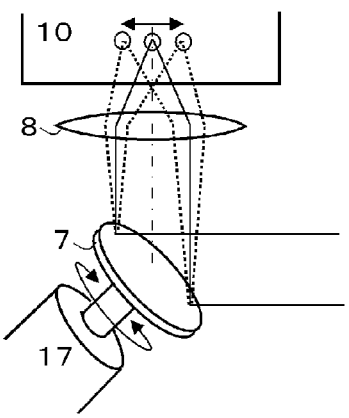
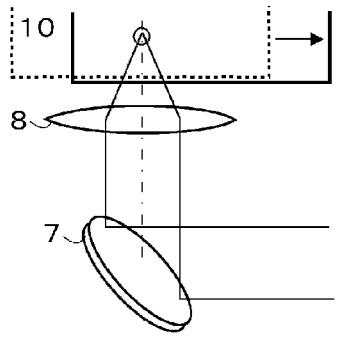

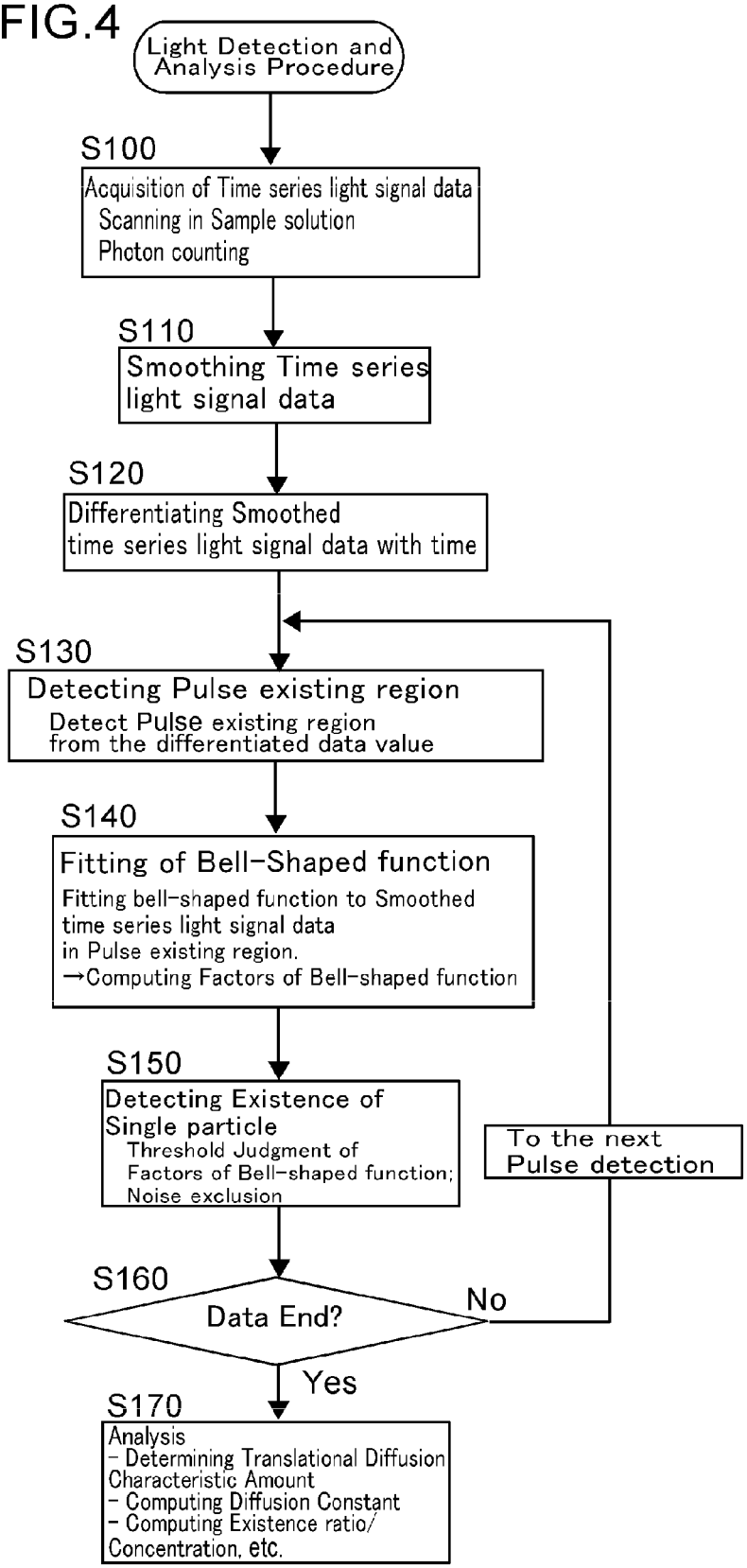

FIG.5C Detected result (unprocessed)
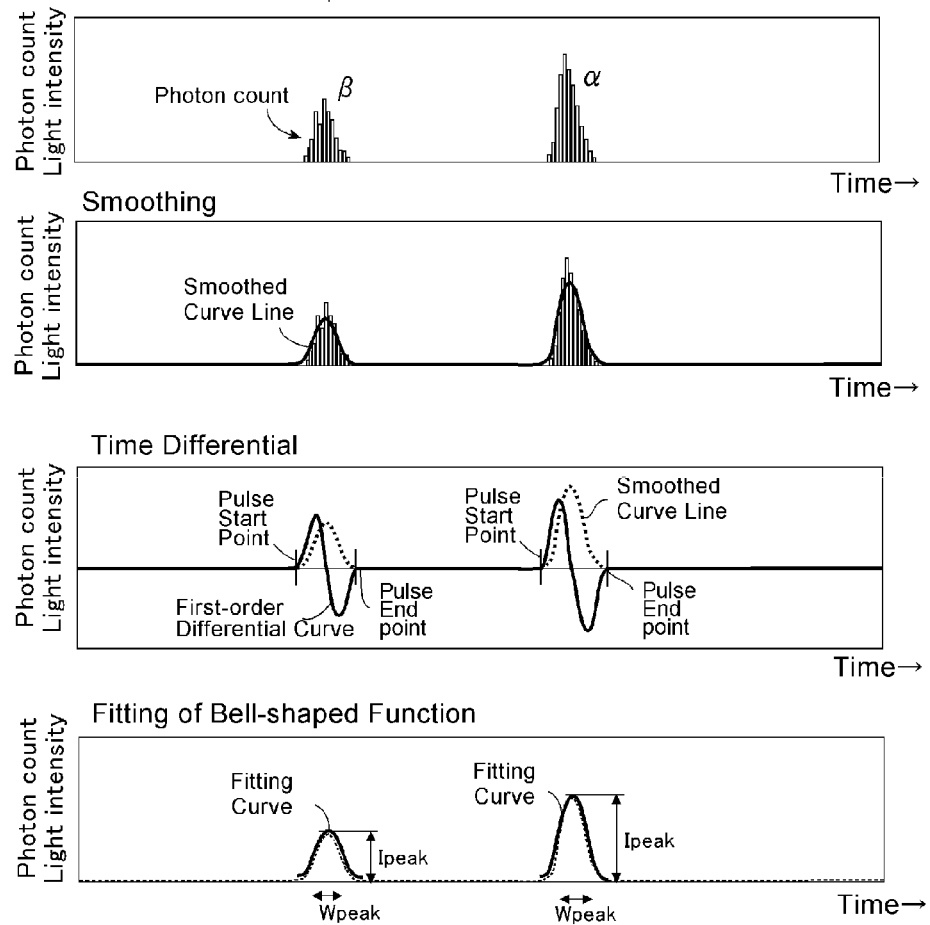

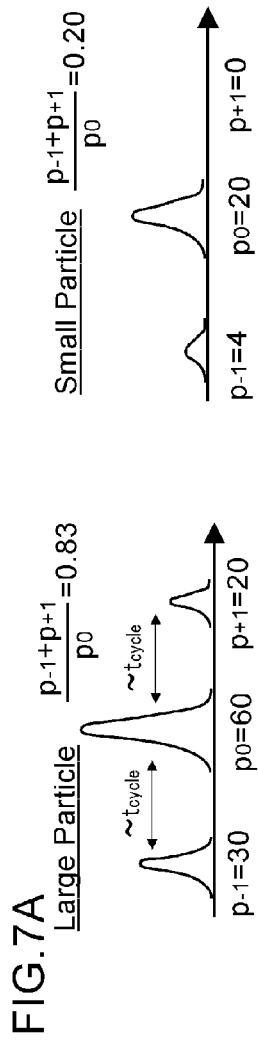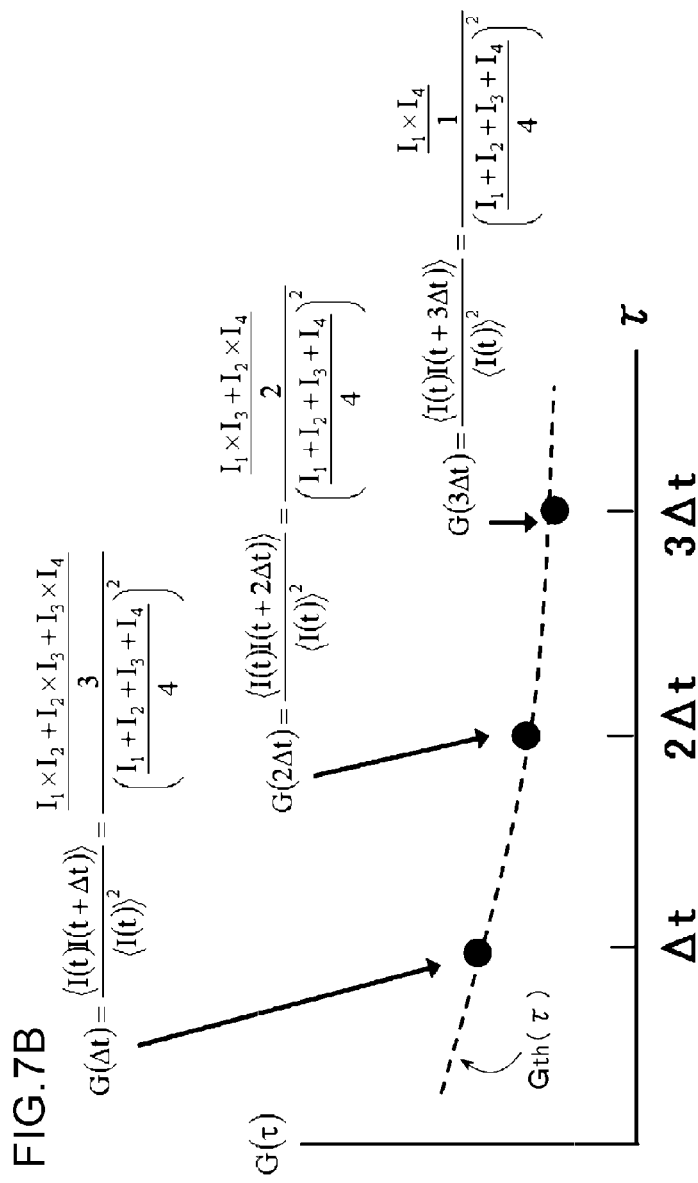
FIG.7A
FIG.7B

FIG.9A Time Variations of Signals
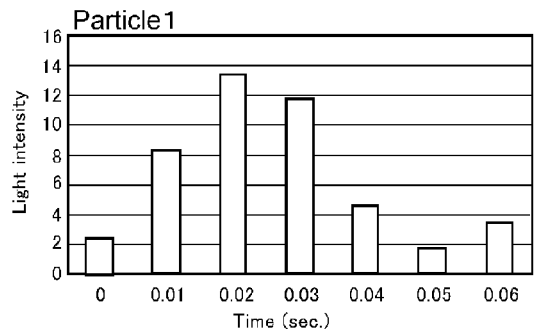
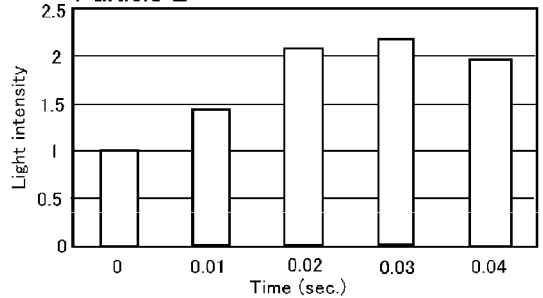
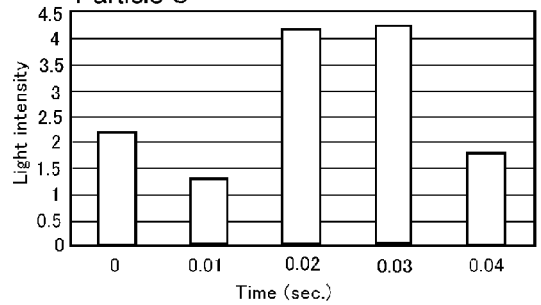
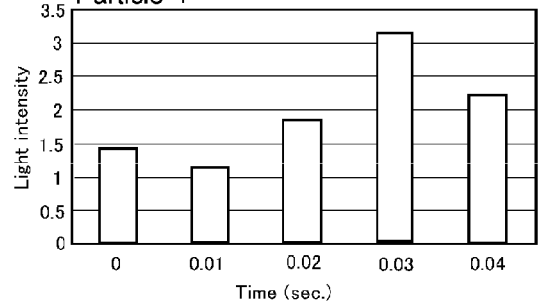
FIG.9B Intensity Autocorrelation Function Values
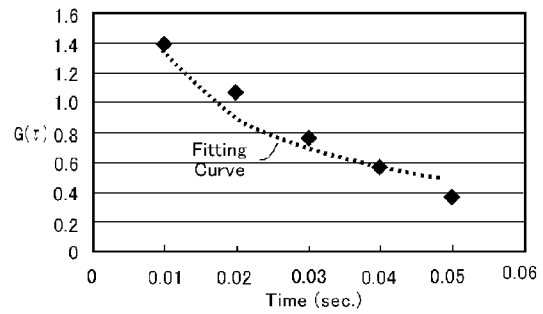
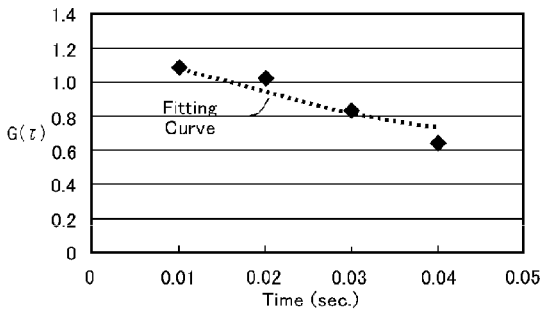
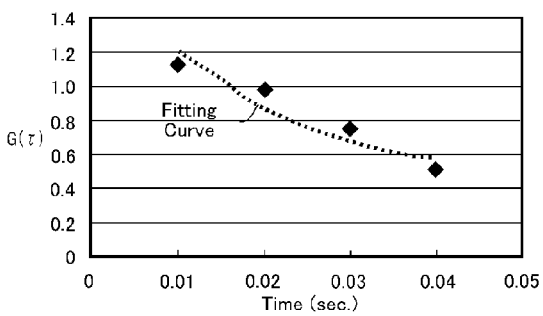
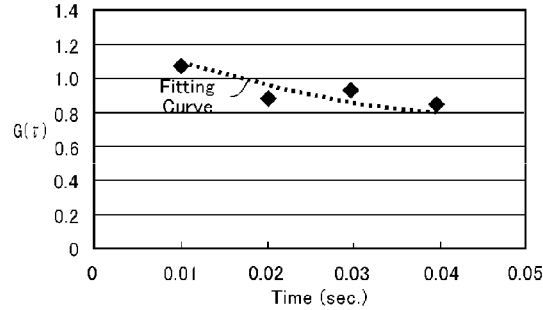

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to an optical analysis device, optical analysis method and computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed optical analysis techniques of performing detection of a characteristic, an intermolecular interaction, a binding or dissociating reaction of a biological molecule, etc. by means of such a faint light measurement technique. As such optical analysis techniques, for examples, there are known Fluorescence Correlation Spectroscopy (FCS, see e.g. patent documents 1-3 and non-patent documents 1-3), Fluorescence Intensity Distribution Analysis (FIDA, e.g. patent document 4, non-patent document 4) and Photon Counting Histogram (PCH, e.g. patent document 5). In addition, in patent documents 6-8, there are proposed methods of detecting fluorescent substances based on a time progress of fluorescence signals of a sample solution measured using the optical system of a confocal microscope.

Furthermore, in patent documents 9-11, Applicant of the present application has proposed a novel optical analysis technique, using an optical system which is capable of detecting the light from a micro region in a solution, such as an optical system of a confocal microscope or a multiphoton microscope, and employing a different principle from optical analysis techniques, such as FCS and FIDA. In the case of optical analysis techniques, such as the above-mentioned FCS, FIDA, briefly speaking, a concentration and/or other characteristics of fluorescence molecules are detected through performing statistical calculation processing of light intensity data obtained by continuously measuring lights from fluorescence molecules floating in a micro region, in which light is detected, in a sample solution (hereafter, called a "light detection region"). On the other hand, in the new optical analysis technique proposed in patent documents 9-11, the position of a light detection region is moved in a sample solution (i.e., the inside of the sample solution is scanned with the light detection region), and when the light detection region encompasses a light-emitting particle being dispersed and moving at random in the sample solution, the light emitted from the light-emitting particle is individually detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter), not only a sample amount necessary for measurement may be small (for example, about several 10 µL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the cases of optical analysis techniques, such as FCS and FIDA. Thus, the "scanning molecule counting method" is expected to be a strong tool enabling an experiment or a test at low cost and/or more quickly than conventional biochemical methods, and also enabling the detection of a concentration and/or a characteristic of a particle of a lower concentration at which FCS, FIDA, etc. cannot be acceptably performed, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446
Patent document 9: WO2011/108369
Patent document 10: WO2011/108370
Patent document 11: WO2011/108371

Non-Patent Documents

Non-patent document 1: Masataka Kinjo; "Protein, Nucleic acid, Enzyme" Vol. 44, No. 9, pages 1431-1438, 1999.

Non-patent document 2: F. J. Meyer-Alms; "Fluorescence Correlation Spectroscopy" edt. R. Rigler, Springer, Berlin, pages 204-224, 2000.

Non-patent document 3: Noriko Kato, et al. "Gene medicine", Vol. 6, No. 2, pages 271-277.

Non-patent document 4: P. Kask, K. Palo, D. Ullmann, K. Gall PNAS 96, 13756-13761 (1999)

Non-patent document 5: R. Rigler, U. Mets, J. Widengren and P. Kask, European Biophysics Journal, 1993, Volume 22, Number 3, Pages 169-175

Non-patent document 6: R. Machan and M. Hof, Int. J. Mol. Sci. 2010, 11, 427-457

SUMMARY OF INVENTION

Technical Problem

By the way, in the above-mentioned scanning molecule counting method, with respect to different kinds of light-emitting particles having a common emission wavelength, it is difficult to distinguish among these kinds mutually, or to conduct "the identification of a light-emitting particle" (specifying or discriminating a kind of light-emitting particle or confirming or determining what kind of light-emitting particle or which light-emitting particle a detected light-emitting particle is), for example, in accordance with the brightnesses of the light-emitting particles (emitted light intensities in the observation under the same condition). As described also in patent documents 9-11, in the case of the scanning molecule counting method, the light emitted from one light-emitting particle appears as a pulse form signal on time series light intensity data when the light-emitting particle passes through a light detection region, and thus, under an assumption that one pulse form signal corresponds to one light-emitting particle, the existence of each light-emitting particle is detected individually by detecting individually a pulse form signal on time series light intensity data. In this structure, typically, the intensity of the detected light emitted from the light detection region of the optical system of a confocal microscope or a multiphoton microscope (the intensity of the light which is emitted from a single light-emitting particle and reaches to a photodetector) varies in accordance with a bell-shaped distribution with the apex at the almost center of the light detection region because of the spatial distribution of excitation light and/or the characteristics of the optical system, and accordingly, even in the same light-emitting particle, the measured, emitted light intensity changes depending upon its position within the light detection region. Then, because the intensity of the light which is emitted from a single light-emitting particle and reaches to a photodetector changes depending upon positions of the light-emitting particle in the light detection region, it is not possible to distinguish between a case of a particle with weak brightness passing through a site of strong excitation light intensity and a case of a particle with strong brightness passing through a site of weak excitation light intensity in accordance with the magnitudes of the emitted light intensities of pulse form signals. Namely, the absolute value of the emitted light intensity measured in the scanning molecule counting method is not an inherent value of a light-emitting particle, and therefore, it is not possible to distinguish among mutually different light-emitting particles having a common emission wavelength but having mutually different brightnesses, using the difference in the emitted light intensities of single light-emitting particles. Thus, in a sample solution containing light-emitting particles of two or more kinds, when these light-emitting particles have a common emission wavelength, it is not possible to detect a light-emitting particle with identifying it by the kind even if the brightnesses of the light-emitting particles differ mutually.

Thus, the main object of the present invention is to provide a novel way of enabling the discrimination or identification of a kind of light-emitting particle corresponding to each pulse form signal in the above-mentioned scanning molecule counting method.

With respect to the above-mentioned object, the inventors of the present invention have found that, in the scanning molecule counting method, when the same light-emitting particle is detected multiple times, the light intensity of its signal changes and this light intensity change is caused by the moving of the light-emitting particle by diffusion. Namely, the light intensity change of the signal during the multiple times measurements reflects the diffusional characteristic of a light-emitting particle, the identification of the light-emitting particle in accordance with the diffusional characteristic is achieved based on the light intensity change of the signal during the multiple times measurements. This knowledge is advantageously used in the present invention.

Solution to Problem

Thus, according to the present invention, the above-mentioned object is achieved by an optical analysis device which detects light from a light-emitting particle dispersed and moving at random in a sample solution using an optical system of a confocal microscope or a multiphoton microscope, comprising: a light detection region mover which moves a position of a light detection region of the optical system of the microscope in the sample solution periodically along a predetermined route; a light detector which detects light from the light detection region; and a signal processor which generates time series light intensity data of the light from the light detection region detected with the light detector during the moving of the position of the light detection region in the sample solution and detects a signal indicating light from a single light-emitting particle individually in the time series light intensity data; wherein the signal processor determines an index value indicating a translational diffusional characteristic of one light-emitting particle in a plane perpendicular to the moving direction of the light detection region based upon an intensity value of a detected signal indicating light of the one light-emitting particle and an intensity value within a time region separated from a generation time of the signal indicating light of the one light-emitting particle by a time corresponding to an integral multiple of a moving cycle of the position of the light detection region in the time series light intensity data.

In the structure of the above-mentioned present invention, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is deter-mined in accordance with the spatial relationship of an objective and a pinhole. For a light-emitting particle which emits light without illumination light, for example, a molecule which emits light according to chemiluminescence or bioluminescence, no illumination light is required in the microscope.). Further, typically, the light detector detects the light from the light detection region by the photon counting in which (a) photon(s) arriving in every predetermined measuring unit time (bin time) is/are counted, and in that case, the time series light intensity data becomes time series photon count data. Further, "a time region separated from a generation time of the signal indicating light of the one light-emitting particle by a time corresponding to an integral multiple of a moving cycle of the position of the light detection region in the time series light intensity data" is a time region obtained by adding to or subtracting from the generation time of the signal indicating light of one certain light-emitting particle a time corresponding to an integral multiple of the moving cycle time of the position of the light detection region. Namely, this time region is the time region in which the detected value of the light at the time when the repetitively circulating light detection region passes through a space where one certain light-emitting particle is present appears (Data mutually corresponding to the same space). In this connection, in this specification, "a signal of a light-emitting particle" means a signal expressing light from a light-emitting particle, unless noted otherwise.

In the basic structure of the above-mentioned present invention, i.e., the scanning molecule counting method, the light detection is sequentially performed while the position of the light detection region is moved in a sample solution, namely, while the inside of the sample solution is scanned with the light detection region. Then, it is expected that, when the light detection region moving in the sample solution encompasses a randomly moving light-emitting particle, the light from the light-emitting particle is detected by the light detector and thereby the existence of one particle will be detected. Thus, in the time series data of the sequentially detected light (time series light intensity data), a signal indicating light from a light-emitting particle is individually detected, and thereby, the existences of individual particles are detected one by one, and accordingly, diverse information on the conditions of the particles in the solution will be acquired.

In this structure, as already noted, since the intensity of light which is emitted from a single light-emitting particle and reaches to a photodetector in the optical analysis device changes depending upon the position of the light-emitting particle in the light detection region, the absolute value of the light intensity of the signal cannot be directly used for the discrimination or identification of kinds of light-emitting particle having a common emission wavelength but having mutually different brightnesses. On the other hand, the change of light intensity of the same light-emitting particle detected when the position of the light detection region circulates along a predetermined route reflects the change of the position by the Brownian motion (translational diffusion moving) of the light-emitting particle within a plane perpendicular to the moving direction of the light detection region during the circulations of the position of the light detection region, and thus, as described in detail later, it becomes possible to acquire the information about the translational diffusional characteristic of the light-emitting particle from the change of the light intensity of the light-emitting particle during the circulating movements of the light detection region. And the translational diffusional characteristic of a light-emitting particle is usable in the discrimination or identification of a kind of the light-emitting particle. Then, in the present invention, in order to detect the translational diffusional characteristic of each light-emitting particle, the light measurement is performed while the position of the light detection region is periodically moved along a predetermined route so that the same light-emitting particle will be detected multiple times. And, with reference to an intensity value of a detected signal indicating light of one light-emitting particle and an intensity value within a time region separated from the generation time of the signal indicating light of the one light-emitting particle by the time corresponding to an integral multiple of the moving cycle of the position of the light detection region in the time series light intensity data, namely, a series of light intensity values of the space in which one light-emitting particle exists during the circulating movements of the light detection region, or the intensity values of a series of signals of the same light-emitting particle during the circulating movements of the light detection region, the index value indicating the translational diffusional characteristic of the light-emitting particle is determined based upon those plural light intensity values, and thereby, it is tried to discriminate or identify the kind of each light-emitting particle. Concretely, the kind of light-emitting particle may be determined according to the index value indicting the translational diffusional characteristic of the light-emitting particle determined as noted above.

In one manner of the above-mentioned structure of the present invention, the index value indicating the translational diffusional characteristic of a light-emitting particle may be, for example, the ratio between the intensity value of the signal of one light-emitting particle and the sum of intensity values within time regions separated by the time corresponding to the moving cycle time of the position of the light detection region before and after the signal of the one light-emitting particle. As shown also in the column of the detailed explanation later, the space, in which a light-emitting particle corresponding to one signal exists, is encompassed by the light detection region in time regions separated by the time corresponding to the moving cycle time of the position of the light detection region before and after the one signal of the light-emitting particle. And, the relation between the intensity value of the signal of one light-emitting particle and the intensity values within time regions separated by the time corresponding to the moving cycle time of the position of the light detection region before and after the signal of the one light-emitting particle, namely, the variation of the light intensity emitted from the same space, reflects the degree of the magnitude of the moving of the light-emitting particle by the Brownian motion during the circulations of the light detection region. That is, the slower the motion of a light-emitting particle is, the smaller the variation between the intensity value of the signal of one light-emitting particle and the intensity values within time regions separated by the time corresponding to the moving cycle time of the position of the light detection region before and after the signal of the one light-emitting particle, namely, the change of the light intensity emitted from the same space during the circulations of the light detection region becomes. Therefore, as noted above, with reference to the ratio between the intensity value of the signal of one light-emitting particle and the sum of intensity values within time regions separated by the time corresponding to the moving cycle time of the position of the light detection region before and after the signal of the one light-emitting particle, the translational diffusional characteristic of a light-emitting particle can be grasped. Practically, as shown in the embodiment described later, it has been found that the ratio between the intensity value of the signal of one light-emitting particle and the sum of intensity values within time regions separated by the time corresponding to the moving cycle time of the position of the light detection region before and after the signal of the one light-emitting particle varies depending upon the degree of the easiness of the translational diffusion of a light-emitting particle. Thus, the ratio of intensity values may be employed as an index value for discrimination or identification of the kind of light-emitting particle.

Moreover, in another manner of the structure of the present invention, the index value indicating the translational diffusional characteristic of a light-emitting particle may be the diffusion constant of the light-emitting particle or its function value. As understood from the above-mentioned explanations, the change of light intensity of the signal of the same light-emitting particle detected in every circulation of the light detection region corresponds to the change of the position of the light-emitting particle during the circulations of the light detection region. And, since an autocorrelation function value in time, computed from the intensity values of the signals of the same light-emitting particle in the respective circulations of the light detection region, is theoretically derived from the translational diffusion model of a single light-emitting particle which has a certain diffusion constant in a plane perpendicular to the moving direction of the light detection region, it is possible to compute the diffusion constant of a single light-emitting particle by fitting a theoretical formula, obtained from the translational diffusion model, to the autocorrelation function values in time of the intensity values of the signals. Then, in the present invention, by using, as intensity values within time regions separated from the generation time of a signal indicating light of one light-emitting particle by a time corresponding to an integral multiple of the moving cycle time of the position of the light detection region in time series light intensity data, the intensity values of signals (generated within the time regions) indicating lights of the same light-emitting particle as the one light-emitting particle, a diffusion constant or its function value is computed by fitting a theoretical formula, derived from a translational diffusion model of a light-emitting particle in a plane perpendicular to the moving direction of the light detection region, to autocorrelation function values in time, computed from the intensity value of the signal indicating light of the one light-emitting particle and the intensity values of the signals indicating lights of the same light-emitting particle as the one light-emitting particle, and thereby the diffusion constant or its function value may be employed as an index value indicating a translational diffusional characteristic of the light-emitting particle for the identification of the light-emitting particle. Namely, since the light-emitting particle signals generated every moving cycle time of the light detection region are the signals of the same light-emitting particle, the diffusion constant or its function value of a light-emitting particle may be determined by fitting a theoretical formula derived from a translational diffusion model to autocorrelation function values of the intensity values of those signals, and then this diffusion constant or its function value may be employed as an index value for identification of the light-emitting particle.

In the processes of the signal processor of the above-mentioned inventive device, the judgment of whether or not one light-emitting particle enters into the light detection region from a signal in the successively detected values from the light detector may be performed based on the profile of the time series signal indicating light detected in the light detector. In this regard, in an embodiment, typically, it may be designed that the entry of one light-emitting particle into a light detection region is detected when a signal with a larger intensity than a predetermined threshold value is detected. More concretely, as explained in the following column of embodiments, usually, the profile of a signal indicating light from a light-emitting particle exhibits a bell-shaped pulse form having an intensity beyond a certain degree in the time series detected values i.e., light intensity data, of the light detector, while the profile of a noise does not form a bell-shaped pulse, or its intensity is small. Then, the signal processor of the inventive device may be designed to detect on time series light intensity data a pulse form signal which has an intensity exceeding a predetermined threshold value as a signal indicating light from a signal light-emitting particle. The "predetermined threshold value" can be experimentally set to an appropriate value.

Furthermore, the object to be detected in the inventive device is the light from a single light-emitting particle, and thus, light intensity is extremely weak, and when one light-emitting particle is a single fluorescent molecule or several molecules, the light is stochastically emitted from the light-emitting particle, so that minute time gaps can be generated in the signal values. If such a gap is generated, the identification of a signal corresponding to the existence of one light-emitting particle will become difficult. Then, the signal processor may be designed to apply smoothing treatment to time series light intensity data so that minute time gaps in signal values can be ignored, and to detect as a signal indicating light from a single light-emitting particle a bell-shaped pulse form signal having an intensity beyond a predetermined threshold value in the smoothed time series light intensity data. In this regard, it becomes very troublesome operation to detect by human eyes, etc. a region where a pulse form signal exists in time series light intensity data. Then, in an embodiment, the signal processor may be designed to determine an existence region of a bell-shaped, pulse form signal in a time differential value of smoothed time series light intensity data, and judge as a signal indicating light from a single light-emitting particle a pulse form signal whose intensity value obtained by fitting a bell shaped function formula to the smoothed time series light intensity data in the existence region of the pulse form signal exceeds beyond a predetermined threshold value, so that the time and effort for detecting regions where a pulse form signal exists by human eyes, etc. can be avoided.

The moving speed of the position of the light detection region in a sample solution in the above-mentioned inventive device may be changeable appropriately based on the characteristics, number density or concentration of a light-emitting particle in the sample solution. Especially, when the moving speed of the light detection region becomes quick, the light amount obtained from one light-emitting particle will be reduced, and thus, in order to measure the light from one light-emitting particle accurately or with sufficient sensitivity, it is preferable that the moving speed of the light detection region can be changed appropriately. Moreover, the moving speed of the position of the light detection region in the sample solution is preferably set to be higher than the diffusional moving velocity of a light-emitting particle to be an object to be detected (the average moving speed of a particle owing to the Brownian motion). As explained above, the inventive device detects a light-emitting particle individually by detecting the light emitted from a light-emitting particle when the light detection region passes through the existence position of the light-emitting particle. However, when the light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of a light-emitting particle, and thereby it becomes possible to make one light-emitting particle associated with one signal. In this regard, since the diffusional moving velocities differ depending upon light-emitting particles, it is preferable that the moving speed of the light detection region can be changed appropriately according to the characteristics (especially, the diffusion constant) of the light-emitting particle as described above.

Furthermore, in the case of the present invention, it is required to be capable of encompassing the same light-emitting particle periodically in the light detection region during multiple times of circulations of the light detection region. Then, preferably, the moving cycle time of the light detection region is set to be shorter than the time taken for a light-emitting particle detected once to move the distance equivalent to the size of the light detection region by the Brownian motion. The moving cycle time of a light detection region can be set by adjusting appropriately the above-mentioned moving speed and predetermined route length.

The moving of the position of the light detection region in a sample solution may be achieved by an arbitrary way. For example, the position of the light detection region may be changed by changing the optical path of the optical system of the microscope using a galvanometer mirror adopted in a laser scan type light microscope, or the position of the sample solution may be moved (e.g. by moving the stage of a microscope) so that the position of the light detection region will be moved in the sample solution. The movement track of the position of the light detection region may be set arbitrarily, for example, may be selected from circular, elliptical, rectangular, straight linear and curvilinear ones. Especially, in the case of changing the position of the light detection region by changing the optical path of the optical system of the microscope, the moving of the light detection region is quick, and since neither mechanical vibration nor hydrodynamic action occurs substantially in the sample solution, it is advantageous in that a measurement can be conducted under a stable condition without a light-emitting particle to be an object to be detected being influenced by a dynamic action.

In one of manners of the above-mentioned present invention, the number of light-emitting particles encompassed in the light detection region may be counted by counting the number of the selectively detected signals (The counting of particles). In that case, by associating the number of the detected light-emitting particles with the moving amount of the position of the light detection region, the information on the number density or concentration of the light-emitting particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the light-emitting particle can be concretely computed.

The processes of the optical analysis technique of conducting a light detection with moving the position of a light detection region in a sample solution and detecting the signal from each light-emitting particle individually in the above-mentioned inventive device, in which the light of the same light-emitting particle is detected multiple times and an index value indicating a translational diffusional characteristic of the light-emitting particle is determined based on the variation of the light intensity, can be realized with a general-purpose computer.

Thus, according to another aspect of the present invention, there is provided a computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising: moving a position of a light detection region of the optical system of the microscope in the sample solution periodically along a predetermined route; measuring a light intensity from the light detection region during the moving of the position of the light detection region in the sample solution to generate light intensity data; detecting individually a signal indicating light from a single light-emitting particle in the light intensity data; and determining an index value indicating a translational diffusional characteristic of one light-emitting particle in a plane perpendicular to the moving direction of the light detection region based upon an intensity value of a detected signal indicating light of the one light-emitting particle and an intensity value within a time region separated from a generation time of the signal indicating light of the one light-emitting particle by a time corresponding to an integral multiple of a moving cycle time of the position of the light detection region in the time series light intensity data. In this regard, the computer program is provided while being memorized in a computer readable storage medium. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program. Further, in the above-mentioned structure, in the step of detecting light from the light detection region to generate time series light intensity data, the light from the light detection region is detected by the photon counting in which the number of photons arriving every measuring unit time (bin time) is counted, and in that case, the time series light intensity data is time series photon count data. Moreover, in this case, there may be included a step of determining the kind of the light-emitting particle with the index value indicating a translational diffusional characteristic of the light-emitting particle.

In the above-mentioned structure also, as the index value indicating the translational diffusional characteristic of a light-emitting particle, the ratio between the intensity value of the signal of one light-emitting particle and the sum of intensity values within time regions separated by the time corresponding to the moving cycle time of the position of the light detection region before and after the signal of the one light-emitting particle may be employed. Or, as an index value indicating a translational diffusional characteristic of a light-emitting particle, there may be employed a diffusion constant or its function value which is computed by fitting a theoretical formula, derived from a translational diffusion model of a light-emitting particle in a plane perpendicular to the moving direction of the light detection region, to autocorrelation function values in time, computed from an intensity value of a signal indicating light of one light-emitting particle and intensity values of signals indicating lights of the same light-emitting particle as the one light-emitting particle, by using, as the intensity values within time regions separated from the generation time of the signal indicating light of the one light-emitting particle by the time corresponding to the integral multiple of the moving cycle time of the position of the light detection region in time series light intensity data, the intensity values of signals generated within the time regions and indicating lights of the same light-emitting particle as the one light-emitting particle.

Further, also in the above-mentioned computer readable storage device, the individual detection of a signal indicating light from each light-emitting particle may be performed based on the profile of the time series signal. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle. And more in detail, in a time differential value of smoothed time series light intensity data, an existence region of a bell-shaped, pulse form signal may be determined, and a pulse form signal whose intensity value obtained by fitting a bell shaped function formula to the smoothed time series light intensity data in the existence region of the pulse form signal exceeds beyond a predetermined threshold value may be judged as a signal indicating light from a signal light-emitting particle.

Furthermore, the moving speed of the position of the light detection region in the sample solution may be appropriately changed based on the characteristics, the number density or concentration of the light-emitting particle in the sample solution, and preferably, the moving speed of the position of the light detection region in the sample solution is set higher than the diffusion moving velocity of the light-emitting particle to be the object to be detected. Also, preferably, the moving cycle time of the position of the light detection region is set to be shorter than the time taken for a light-emitting particle detected once to move the distance equivalent to the size of the light detection region by the Brownian motion. The moving of the position of the light detection region in the sample solution may be conducted by an arbitrary way, and preferably, the position of the light detection region may be changed by changing the optical path of the optical system of the microscope or by moving the position of the sample solution. The movement track of the position of the light detection region may be set arbitrarily, for example, selected from circular, elliptical, rectangular, straight linear, and curvilinear ones.

Also in this computer readable storage device, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

According to the above-mentioned inventive device or computer program, there is realized a novel optical analysis method of conducting detection of the light of each light-emitting particle with moving the position of a light detection region in a sample solution, in which the light of the same light-emitting particle is detected multiple times and an index value indicating a translational diffusional characteristic of the light-emitting particle is determined based on the variation of the light intensity.

Thus, according to the present invention, there is further provided an optical analysis method of detecting light from a light-emitting particle dispersed and moving at random in a sample solution using an optical system of a confocal microscope or a multiphoton microscope, comprising steps of: moving a position of a light detection region of the optical system of the microscope in the sample solution periodically along a predetermined route; measuring a light intensity from the light detection region during the moving of the position of the light detection region in the sample solution to generate light intensity data; detecting individually a signal indicating light from a single light-emitting particle in the light intensity data; and determining an index value indicating a translational diffusional characteristic of one light-emitting particle in a plane perpendicular to the moving direction of the light detection region based upon an intensity value of a detected signal indicating light of the one light-emitting particle and an intensity value within a time region separated from a generation time of the signal indicating light of the one light-emitting particle by a time corresponding to an integral multiple of a moving cycle time of the position of the light detection region in the time series light intensity data. Even in this method, typically, in the step of detecting light from the light detection region to generate time series light intensity data, the light from the light detection region is detected by the photon counting in which the number of photons arriving every measuring unit time (bin time) is counted, and in that case, the time series light intensity data is time series photon count data. Moreover, also in this case, there may be included a step of determining the kind of the light-emitting particle with the index value indicating a translational diffusional characteristic of the light-emitting particle.

Then, in the above-mentioned structure also, as the index value indicating the translational diffusional characteristic of a light-emitting particle, the ratio between the intensity value of the signal of one light-emitting particle and the sum of intensity values within time regions separated by the time corresponding to the moving cycle time of the position of the light detection region before and after the signal of the one light-emitting particle may be employed. Or, as an index value indicating a translational diffusional characteristic of a light-emitting particle, there may be employed a diffusion constant or its function value which is computed by fitting a theoretical formula, derived from a translational diffusion model of a light-emitting particle in a plane perpendicular to the moving direction of the light detection region, to autocorrelation function values in time, computed from an intensity value of a signal indicating light of one light-emitting particle and intensity values of signals indicating lights of the same light-emitting particle as the one light-emitting particle, by using, as the intensity values within time regions separated from the generation time of the signal indicating light of the one light-emitting particle by the time corresponding to the integral multiple of the moving cycle time of the position of the light detection region in time series light intensity data, the intensity values of signals generated within the time regions and indicating lights of the same light-emitting particle as the one light-emitting particle.

Further, also in the above-mentioned method, the individual detection of a signal indicating light from each light-emitting particle may be performed based on the profile of the time series signal. In one embodiment, typically, it may be designed that the entry of one light-emitting particle into the light detection region is detected when a signal with a larger intensity than a predetermined threshold value is detected. Concretely, a bell-shaped pulse form signal having an intensity beyond a predetermined threshold value in light intensity data may be detected as a signal indicating light from a single light-emitting particle, and preferably, the time series light intensity data may be smoothed so that a bell-shaped pulse form signal having an intensity beyond a predetermined threshold value in the smoothed time series light intensity data may be detected as a signal indicating light from a single light-emitting particle. And more in detail, in a time differential value of smoothed time series light intensity data, an existence region of a bell-shaped, pulse form signal may be determined, and a pulse form signal whose intensity value obtained by fitting bell shaped function formula to the smoothed time series light intensity data in the existence region of the pulse form signal exceeds beyond a predetermined threshold value may be judged as a signal indicating light from a single light-emitting particle.

Furthermore, the moving speed of the position of the light detection region in the sample solution may be appropriately changed based on the characteristics, the number density or concentration of the light-emitting particle in the sample solution, and preferably, the moving speed of the position of the light detection region in the sample solution is set higher than the diffusion moving velocity of the light-emitting particle to be the object to be detected. The moving of the position of the light detection region in the sample solution may be conducted by an arbitrary way, and preferably, the position of the light detection region may be changed by changing the optical path of the optical system of the microscope or by moving the position of the sample solution. The movement track of the position of the light detection region may be set arbitrarily, for example, selected from circular, elliptical, rectangular, straight linear, and curvilinear ones.

Also in the above-mentioned method, there may be comprised a step of counting the number of the light-emitting particles detected during the moving of the position of the light detection region by counting the number of the signals from the light-emitting particles detected individually and/or a step of determining the number density or concentration of the light-emitting particle in the sample solution based on the number of the detected light-emitting particles.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, according to the present invention, discrimination or identification of a kind of light-emitting particle can be achieved with a translational diffusional characteristic of a light-emitting particle in the scanning molecule counting method. In the way of the present invention, for instance, no such a process of preparing light-emitting particles having different emission wavelengths by kinds of particles is required, and this is advantageous in the detection of the existence of a sample solution containing two or more kinds of light-emitting particle, the determination of their concentrations, etc.

By the way, in a case that a sample solution contains two or more kinds of light-emitting particle, it is possible to distinguish among mutually different kinds of light-emitting particles having a common emission wavelength by the conventional FCS and FIDA also. In the case of FCS, there is computed a translational diffusion time indicating the diffusional characteristic of a particle, and thus, even in a sample solution in which light-emitting particles of two or more kinds having different diffusional characteristics are mixed, it is possible to estimate the ratio and concentrations of two or more kinds of light-emitting particles by referring to translational diffusion times. Further, in the case of FIDA, the average emitted light intensity per single light-emitting particle is computed, and thus, even in a sample solution in which light-emitting particles of two or more kinds having different brightnesses are mixed, it is possible to estimate the ratio and concentrations of light-emitting particles of the respective kinds. Regarding this advantage, the present invention is the same, but, it should be understood that, in the case of the present invention, the diffusional characteristic is grasped for each single light-emitting particle, and thereby, the identification is possible for each light-emitting particle. Moreover, in the present invention, the identification of a light-emitting particle is achieved for light-emitting particles of substantially lower concentration than in the case of FCS or FIDA. According to this advantage, even in a case that a small number of light-emitting particles of two or more kinds are contained in a sample solution, the individual existences or concentrations of the respective light-emitting particles can be detected.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the scanning molecule counting method according to the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution. FIG. 1D is a schematic diagram of the mechanism which moves the horizontal position of a micro plate to move the position of the light detection region in a sample solution.

Figure 2B:
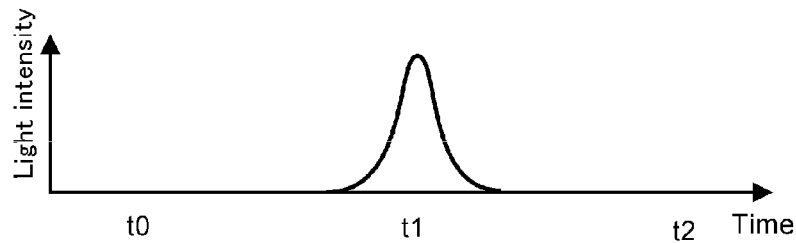
Figure 2C:
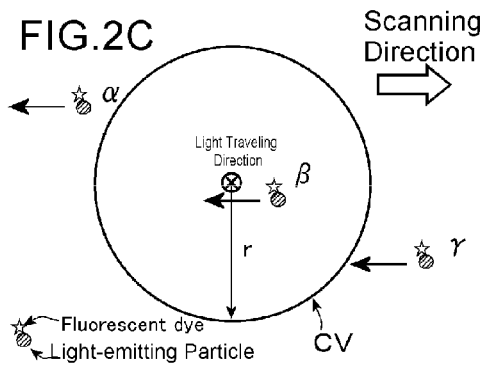
Figure 2D:
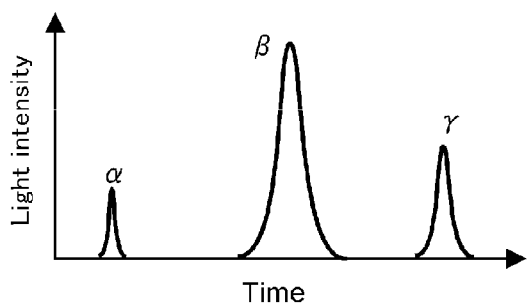
Figure 2E:
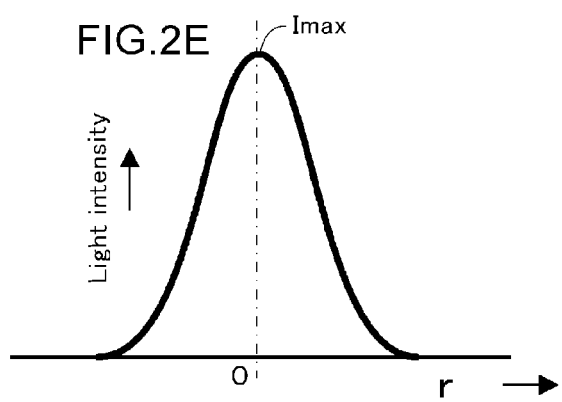

FIGS. 2A and 2B are a schematic diagram explaining the principle of the light detection and a schematic diagram of the variation of the measured light intensity with time in the scanning molecule counting method to which the present invention is applied, respectively. FIG. 2C is a sectional schematic view of the light detection region seen in the traveling direction of the light of a microscope, showing schematically light-emitting particles passing through the inside of the light detection region CV. FIG. 2D is a schematic diagram of an example of the time series light intensity data measured in FIG. 2C. FIG. 2E shows a spatial distribution of the intensity of detected light which is emitted from a light-emitting particle in a light detection region.

Figure 3A:
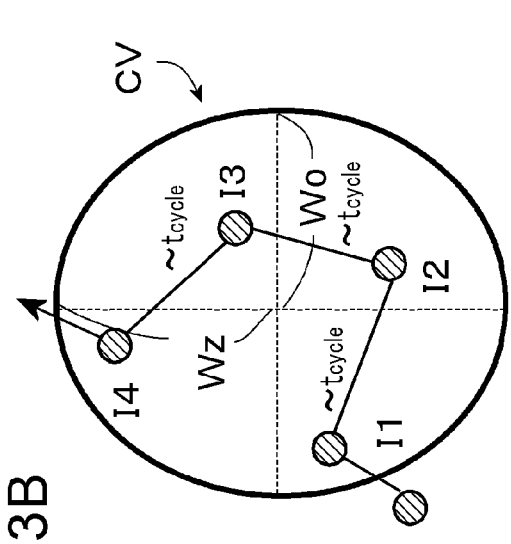
Figure 3B:
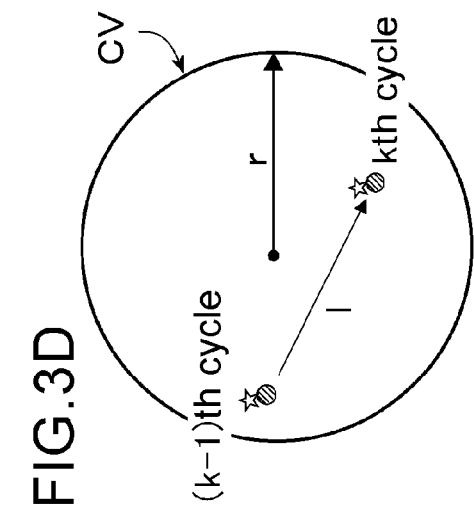
Figure 3C:
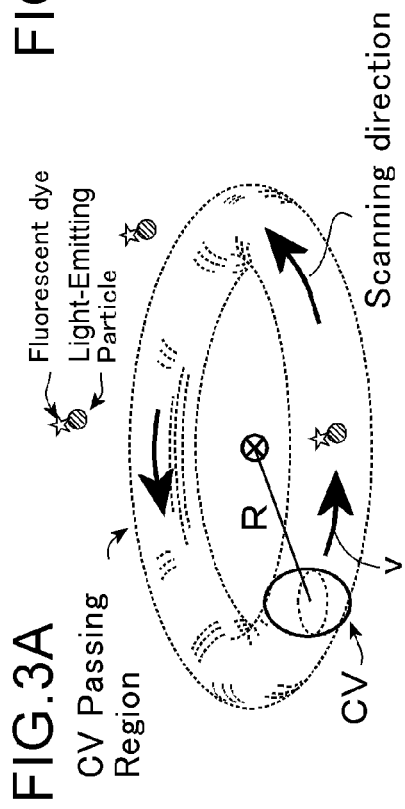
Figure 3D:
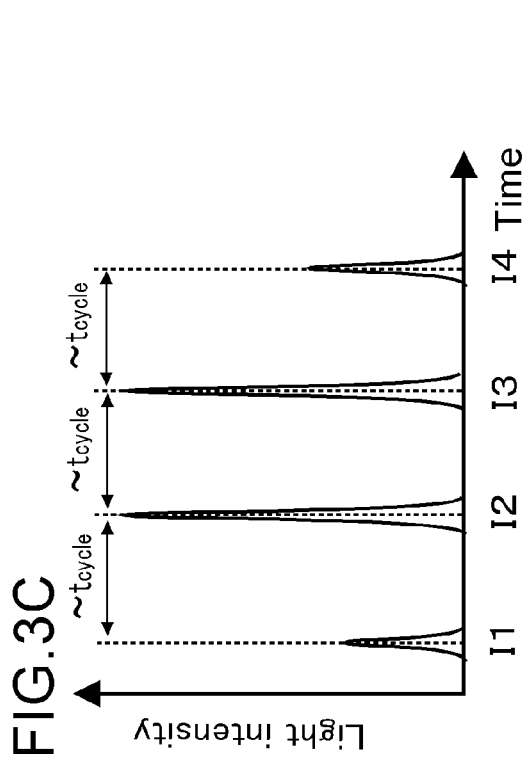

FIG. 3A is a schematic perspective diagram of a spatial region encompassed by moving of a light detection region CV of a microscope along a predetermined route in a sample solution. FIG. 3B is a diagram showing schematically an example of the motion of a light-emitting particle within a plane perpendicular to the moving direction of a light detection region during the circulations of the light detection region. FIG. 3C is a graph showing schematically the intensity, against time, of light from a light-emitting particle detected when the light-emitting particle hardly moves while a light detection region circulates through a predetermined route. FIG. 3D is a schematic diagram of a light detection region explaining the relation between the size of the light detection region and the displacement (per one circulation of the light detection region) of a light-emitting particle by the Brownian motion.

FIG. 4 is a drawing showing in the form of a flow chart procedures of the scanning molecule counting method performed according to the present invention.

Figure 5A:
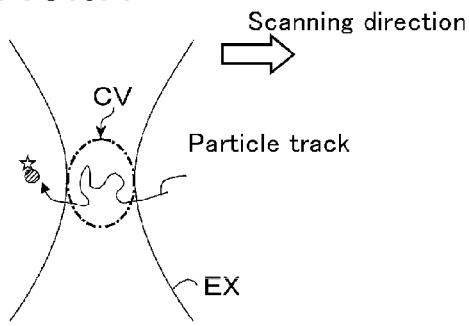
Figure 5B:
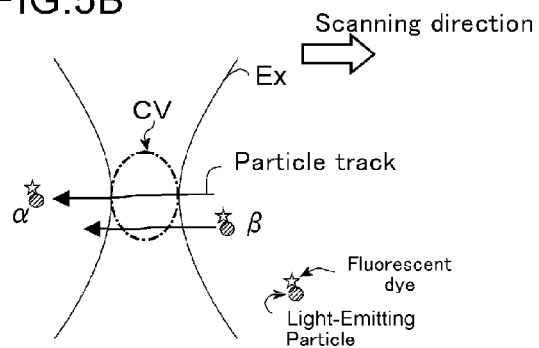

FIGS. 5A and 5B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 5C shows drawings explaining an example of the signal processing step of the detected signals in the procedure for detecting the existence of a light-emitting particle from the measured time series light intensity data (change in time of photon count) in accordance with the scanning molecule counting method.

Figure 6:
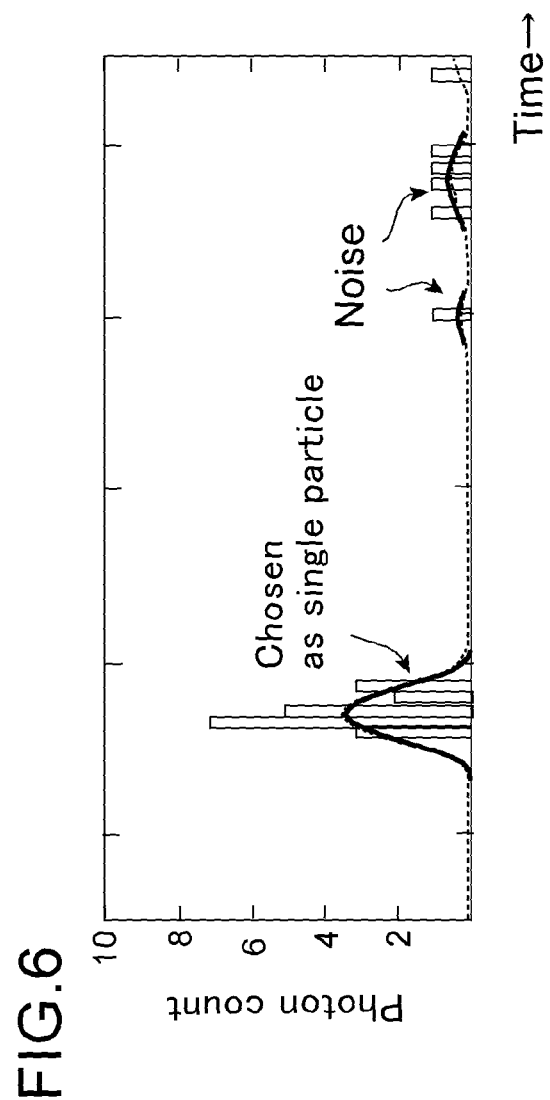

FIG. 6 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or contaminants.

FIG. 7A is drawings explaining the processes for determining the translational diffusion characteristic amount (the ratio between a signal intensity of one light-emitting particle and the sum of light intensity values in the times before and after one circulation of a light detection region) in accordance with the present invention. FIG. 7B shows a formula of an autocorrelation function of light intensity, plots and a fitting curve, which are computed for computation of the diffusion constant of a light-emitting particle in accordance with the present invention.

Figure 8A:
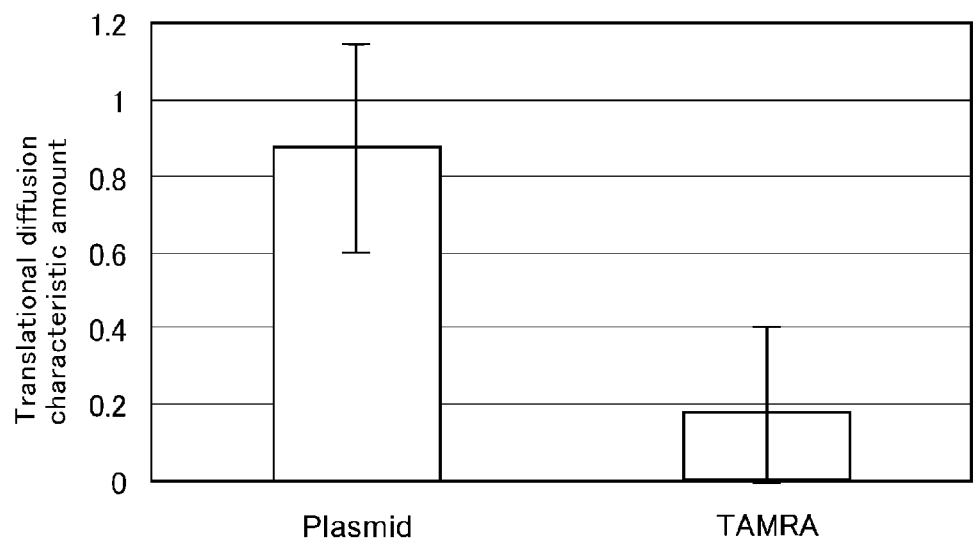
Figure 8B:
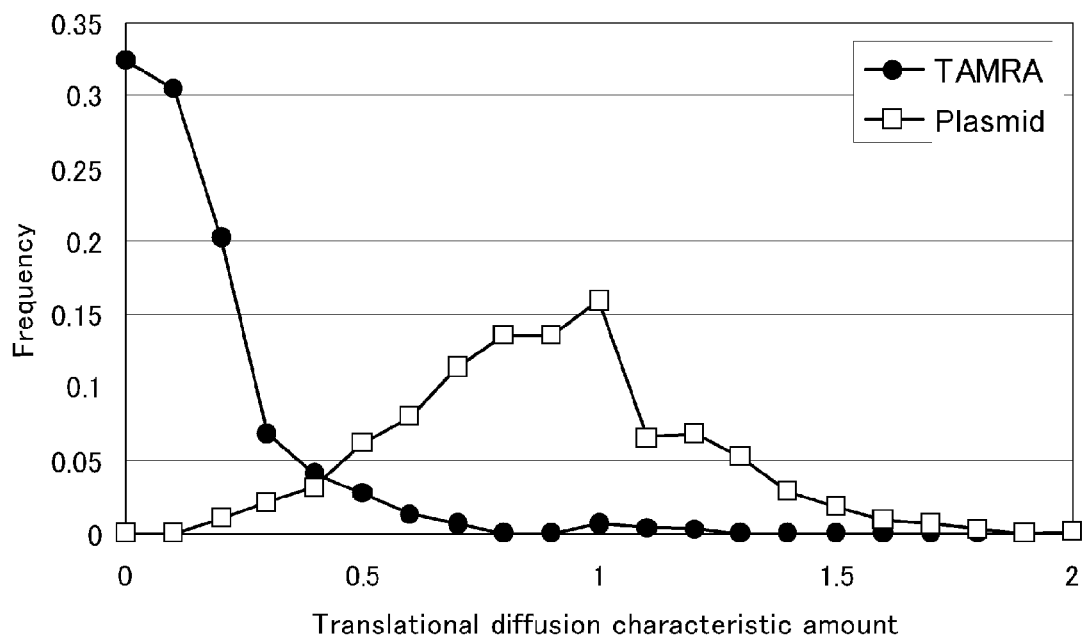

FIG. 8A is a drawing showing in the form of graphs the average values of the translational diffusion characteristic amounts of a plasmid and a fluorescent dye (TAMRA), measured in accordance with the scanning molecule counting method improved in accordance with the present invention (Embodiment 1), and FIG. 8B is a drawing showing the histogram (frequencies) of the translational diffusion characteristic amounts of FIG. 8A in the form of graph charts.

FIG. 9 each shows examples of signal intensities (FIG. 9A) and autocorrelation function values and fitting curves (FIG. 9B) of the same light-emitting particles, measured in accordance with the scanning molecule counting method improved in accordance with the present invention (Embodiment 2).

EXPLANATION OF REFERENCE NUMERALS

1—Optical analysis device (confocal microscope)
2—Light source
3—Single mode optical fiber
4—Collimating lens
5—Dichroic mirror
6, 7, 11—Reflective mirror
8—Objective
9—Micro plate
10—Well (sample solution container)
12—Condenser lens
13—Pinhole
14—Barrier filter
14a—Dichroic mirror
15—Multi-mode optical fiber
16—Photodetector
17—Mirror deflector
17a—Stage position changing apparatus
18—Computer

DESCRIPTION OF EMBODIMENTS

In the followings, preferable embodiments of the present invention are described in detail.

Structure of Optical Analysis Device

In the basic structure, an optical analysis device which realizes the optical analysis technique according to the present invention is a device constructed by associating the optical system of a confocal microscope and a photodetector, enabling FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically fluorescent particles or particles to which a light emitting label such as a fluorescent dye is attached, are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through the barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian type distribution having the peak at the center of the region. The effective volume is a volume of an approximate ellipsoid bordering a surface where the light intensity is reduced to $1/e^2$ of the center light intensity), which focal region is called as "confocal volume". Furthermore, in the present invention, since the light from a single light-emitting particle, for example, the faint light from one fluorescent dye molecule is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every measuring unit time (BIN TIME). Thus, in this case, the time series light intensity data is time series photon count data. Also, on the stage (not shown) of the microscope, there may be provided a stage position changing apparatus 17*a* for moving the horizontal position of the micro plate 9, in order to change the well 10 to be observed. The operation of the stage position changing apparatus 17*a* may be controlled by the computer 18. According to this structure, quick measurement can be achieved even when there are two or more specimens.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of moving the absolute position of a light detection region). This mirror deflector 17 may be the same as that of a galvanomirror device equipped on a usual laser scan type microscope. Or, alternatively, as illustrated in FIG. 1D, the stage position changing apparatus 17*a* may be operated in order to move the horizontal position of the container 10 (micro plate 9), into which the sample solution has been dispensed, to move the relative position of the light detection region in the sample solution (the type of moving the absolute position of a sample solution). In either of the ways, in order to attain a desired moving pattern of the position of the light detection region, the mirror deflector 17 or the stage position changing apparatus 17*a* is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.) In this regard, although not illustrated, the position of the light detection region may be moved in the vertical direction by moving the objective 8 or stage up and down.

In the case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may be provided, and thereby, it may be designed that, when two or more kinds of light-emitting particles having different emission wavelengths are included in the sample, the light therefrom can be detected separately in accordance with the wavelengths. Moreover, with respect to the light detection, it may be designed to use light, polarized in a predetermined direction, as excitation light and select, as the detected lights, components in the direction vertical to the polarization direction of the excitation light. In that case, a polarizer (not shown) is inserted in an excitation light optical path, and a polarization beam splitter 14*a* is inserted in a detected light optical path. According to this structure, it becomes possible to reduce the background light in the detected light substantially.

The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disk, a magnetic optical disk, a CD-ROM, a DVD-ROM, a semiconductor memory, etc. Furthermore, the above-mentioned program may be distributed to a computer through communication line, and the computer which has received this distribution may be made to execute the program.

The Principle of the Inventive Method

As described in the column of "Summary of Invention", briefly, in the inventive optical analysis technique, the position of a light detection region is periodically moved along a predetermined route while the light of the same light-emitting particle is detected multiple times in the scanning molecule counting method, and thereby, it becomes possible to distinguish or identify the kind of each light-emitting particle by means of an index value indicating the translational diffusional characteristic of a light-emitting particle determined based on the variation of the light intensity. In the following, the principle of the scanning molecule counting method and the computation of an index value indicating a translational diffusional characteristic in the present invention are explained about.

1. Principle of Scanning Molecule Counting Method

In the basic processes performed in the scanning molecule counting method, as described in patent documents 9-11, briefly speaking, the light detection is performed together with moving the position of the light detection region CV in a sample solution, namely, scanning the inside of the sample solution with the light detection region CV by driving the mechanism (mirror deflector 17) for moving the position of the light detection region to change the optical path or by moving the horizontal position of the container 10 (micro plate 9) into which the sample solution is dispensed, as schematically drawn in FIG. 2A. Then, for example, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in conventional FCS, FIDA, etc.

By the way, in a light detection region of an optical system of confocal microscope or multiphoton microscope as described above, the intensity of light, which is emitted from a light-emitting particle which passes through a light detection region, and reaches to the photodetector, varies depending upon the position of the light-emitting particle within the light detection region CV, owing to the intensity distribution of the excitation light in the light detection region and/or characteristics of the optical system from the objective through the pinhole to the photodetector. Typically, as illustrated in FIG. 2E, the distribution of the intensity of light which is emitted from a light detection region and reaches to a photodetector has its maximum at the almost center of the light detection region (light condensing region) (hereafter, the point of the maximum intensity is referred to as the "maximum intensity point".), forming a bell shaped distribution to the radial direction distances from the maximum intensity point (radii r). Namely, the detected light intensities of light-emitting particles, even having the same brightness (light-emitting particles emitting the substantially equal light intensity in the observation under the same condition), mutually differ depending upon their passing positions. For example, when the light-emitting particles α, β and γ of the same brightness each cross the light detection region CV in the indicated positions as shown in FIG. 2C, the light intensity of the light-emitting particle β which passes through the almost center of the light detection region becomes higher than the light intensities of the light-emitting particles α and γ (see FIG. 2D). Thus, the absolute intensity value of the signal of a light-emitting particle cannot be considered to be a peculiar value of the light-emitting particle, and accordingly, the difference of intensity values cannot be used for discrimination or identification of the kind of the light-emitting particle as it is.

2. Detection of Translational Diffusional Characteristic of a Light-Emitting Particle Although the absolute intensity value of the signal of a light-emitting particle is not usable in discrimination or identification of the kind of light-emitting particle as it is as noted above, the variation of the intensity value of the signal of the same light-emitting particle reflects the change of the position of the light-emitting particle as noted in the column of "Summary of Invention". The changing of the position of a light-emitting particle is caused by the Brownian motion of the light-emitting particle, and the changing speed of the position is dependent on the translational diffusional characteristic of the light-emitting particle. Thus, in the present invention, the variation of the intensity of the signal of the same light-emitting particle is detected during the circulating movements of the position of the light detection region, and it is tried to compute from the variation in the signal of the same light-emitting particle the index value showing the translational diffusional characteristic of the light-emitting particle and use it for discrimination or identification of the kind of the light-emitting particle.

Concretely, first, as schematically drawn in FIG. 3A, a light detection region (CV) is made to circulate in a sample solution so as to pass through a predetermined route (for example, a ring of radius R). In that case, the moving cycle time (tcycle) of the light detection region is adjusted such that, before a once detected light-emitting particle (a light-emitting particle once encompassed in the light detection region) deviates from the spatial domain through which the light detection region passes, the light detection region will reach to the space in which the light-emitting particle was detected. Then, during the light detection region circulating the predetermined route, as long as the same light-emitting particle exists in the spatial domain through which the light detection region passes, its signal will be detected periodically, corresponding to the moving cycle time tcycle of the light detection region, as shown in FIG. 3C, and the signal intensity varies with the position of the light-emitting particle, corresponding to the moving of the position of the light-emitting particle by the Brownian motion (see FIG. 3B). And, the quicker the change of the position of a light-emitting particle, i.e., its motion, is, the larger the change of the signal intensity becomes, and thus, the translational diffusional characteristic of a light-emitting particle will be determined from the change of the signal intensity. A concrete computation process of the index value indicating the translational diffusional characteristic of a light-emitting particle is described later.

By the way, in a case that the diffusion constant of a light-emitting particle is so large that the (average) displacement of the light-emitting particle in the moving cycle time tcycle of the light detection region will exceed beyond the size of the light detection region, it would be difficult to catch the signal of the same light-emitting particle in every circulation of the light detection region. This is because, although the light-emitting particle once encompassed in the light detection region is encompassed again in the light detection region after a circulation of the light detection region when the moving direction of the light-emitting particle extends coincidentally along the passage region (predetermined route) of the light detection region, it is highly probable that a light-emitting particle, after encompassed in the light detection region once, deviates from the passage region of the light detection region and is no longer again encompassed in the light detection region after the circulation of the light detection region when the (average) displacement of the light-emitting particle during one cycle time of the light detection region is so large to exceed beyond the size of the light detection region since the light-emitting particle moves in the random directions. Accordingly, in order to capture periodic signals for achieving certainly the computation of the above-mentioned diffusion constant D, it is preferable that the moving cycle time tcycle of a light detection region is adjusted such that the (three dimensional) displacement 1 of a light-emitting particle in the moving cycle time tcycle of the light detection region will not exceed beyond the diameter 2r of the light detection region as illustrated in FIG. 3D. Namely, in a case of measuring a diffusion constant by the inventive method, preferably, the moving cycle time tcycle of a light detection region is adjusted to satisfy:

$$(2r)^2 > 2 \delta \cdot D \cdot tcycle \tag{1}$$

(where δ is the number of dimensions, and here, δ=3.) In this regard, in an actual measurement, the moving cycle time tcycle of a light detection region may be adjusted so that the condition of the above-mentioned expression (1) will be satisfied with the diffusion constant expected in a light-emitting particle to be tested.

Operation Processes of Scanning Molecule Counting Method

In the embodiment of the scanning molecule counting method in accordance with the present invention with the optical analysis device 1 as illustrated in FIG. 1A, concretely, there are conducted (1) a preparation of a sample solution containing light-emitting particles; (2) a process of measuring the light intensity of the sample solution; (3) a process of detecting light-emitting particle signals; and (4) a process of computing an index value indicating the translational diffusional characteristic of a light-emitting particle. FIG. 4 shows the processes in this embodiment in form of the flow chart.

(1) Preparation of a Sample Solution

The particle to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. When the particle to be an observed object is a particle which emits no light, there is used a particle to which a light emitting label (a fluorescence molecule, a phosphorescence molecule, and a chemiluminescent or bioluminescent molecule) is attached in an arbitrary manner. Typically, the sample solution is an aqueous solution, but not limited to this, and it may be an organic solvent or other arbitrary liquids.

(2) Measurement of Light Intensity of a Sample Solution (FIG. 4—step 100)

The measurement of the light intensity in the optical analysis by the scanning molecule counting method of the present embodiment may be conducted in a manner similar to a measurement process of light intensity in FCS or FIDA except that the mirror deflector 17 or the stage position changing apparatus 17a is driven to move the position of the light detection region within the sample solution (scanning the sample solution) during the measurement. In the operation processes, typically, after dispensing a sample solution into the well(s) 10 of the micro plate 9 and putting it on the stage of the microscope, when a user inputs to the computer 18 a command of starting a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 or the stage position changing apparatus 17a drives the mirror 7 (galvanomirror) or the micro plate 9 on the stage of the microscope to move the position of the light detection region in the well 10, and simultaneously with this, the photodetector 16 sequentially converts the detected light into electric signals and transmits them to the computer 18, which generates the time series light intensity data from the transmitted signals and stores them in an arbitrary manner. In this regard, the photodetector 16 is typically a super high sensitive photodetector which can detect an arrival of a single photon, and thus when the detection of light is performed by the photon counting, the time series light intensity data may be time series photon count data. The bin time in the photon counting is set appropriately so that the feature of the bell shaped profile of a signal will not be lost.

With respect to the moving speed of the position of the light detection region, in the scanning molecule counting method, generally, in order to perform quantitatively precisely individual detection of a light-emitting particle to be observed from the measured time series light intensity data, preferably, the moving speed of the position of the light detection region during light intensity measurement is set to a value quicker than the moving speed in the random motion, i.e., the Brownian motion of a light-emitting particle. When the moving speed of the position of the light detection region is slower than the movement of a particle owing to the Brownian motion, the particle moves at random in the region as schematically drawn in FIG. 5A, whereby the light intensity changes at random, so that it would become difficult to determine a significant light intensity change corresponding to each light-emitting particle (a signal indicating light from a light-emitting particle). Then, preferably, as drawn in FIG. 5B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost similar in the time series light intensity data (When a particle passes through the light detection region in an approximately straight line, the profile of the light intensity change is similar to the excitation light intensity distribution. See FIG. 5C, upper row.) and the correspondence between each light-emitting particle and light intensity can be easily determined.

Concretely, the time $\Delta\tau$ required for a light-emitting particle having a diffusion coefficient D to pass through the light detection region of radius r (confocal volume) by the Brownian motion is given from the equation of the relation of mean-square displacement:

$$(2r)^2 = 6D \cdot \Delta\tau \qquad (2)$$

as:

$$\Delta\tau = (2r)^2/6D \qquad (3),$$

and thus, the velocity of the light-emitting particle moving by the Brownian motion (diffusional moving velocity) Vdif, becomes approximately $$Vdif = 2r/\Delta\tau = 3D/r \qquad (4)$$

Then, with reference to this, the moving speed of the position of the light detection region may be set to a value sufficiently quicker than Vdif. For example, when the diffusion coefficient of a light-emitting particle is expected to be about $D=2.0\times10^{-10}$ m$^2$/s, Vdif will be $1.0\times10^{-3}$ m/s, supposing r is about 0.62 μm, and therefore, the moving speed of the position of the light detection region may be set to its 10 times or more, 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

(3) Individual Detection of a Signal of a Light-Emitting Particle (Steps 110-160)

When the time series light intensity data has been generated, first, the process of detecting (a) signal(s) of (a) light-emitting particle(s) individually on the light intensity data. As already noted, when the track of one light-emitting particle in its passing through the light detection region is approximately straight as shown in FIG. 5B, the light intensity variation in the signal corresponding to the particle in the time series light intensity data has a bell shaped profile reflecting the light intensity distribution in the light detection region determined by the optical system. Thus, basically in the scanning molecule counting method, when the time width Δτ for which the light intensity value exceeding an appropriately set threshold value Ith continues on the light intensity data is in a predetermined range, the signal having the profile of the light intensity may be judged to correspond to one particle having passed through the light detection region, and thereby one light-emitting particle is detected. And a signal whose light intensity has not exceed beyond the threshold value Ith or whose time width Δτ is not within the predetermined range is judged as noise or a signal of a contaminant. Further, when the light intensity distribution in the light detection region can be assumed as a Gaussian distribution:

$$I = A \cdot \exp(-2t^2/a^2) \quad (5),$$

and when the intensity A and the width a, computed by fitting Expression (5) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As one example of the processes of detection of (a)signal(s) on the light intensity data, first, a smoothing treatment is performed to the light intensity data (FIG. 5C, the most upper row "detected result (unprocessed)") (FIG. 4—step 110, FIG. 5C mid-upper row "smoothing"). Although the light emitted by a light-emitting particle is stochastic so that minute time gaps will be generated in data values, such gaps in the data values can be disregarded by the smoothing treatment. The smoothing treatment may be done, for example, by the moving average method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the light intensity data after the smoothing treatment, in order to detect a time domain (pulse existing region) in which a significant pulse form signal (referred to as "pulse signal" hereafter) exists, the first differentiation value with time of the smoothed light intensity data is computed (step 120). As illustrated in FIG. 5C, the mid-low row "time differential", in the time differential value of light intensity data, the value variation increases at the time of the signal value change, and thereby, the start point and the end point of a significant signal can be determined advantageously by referring to the time differential value.

After that, significant pulse signals are detected sequentially on the light intensity data (Steps 130-160). Concretely, first, on the time-differential value data of the light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed light intensity data in the pulse existing region (FIG. 5C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function as in Expression (5), it may be Lorentz type function. Then, it is judged whether or not the computed parameters of the bell shaped function are within the respective ranges assumed for the parameters of the bell-shaped profile drawn by a pulse signal to be detected when one light-emitting particle passes through the light detection region, namely, whether or not the peak intensity, pulse width and correlation coefficient of a pulse are in the respective predetermined ranges, etc.: For example, whether or not the following conditions are satisfied:

20 μsec.<pulse width<400 μsec.

Peak intensity>1.0[pc/10 μsec.]     (A)

Correlation coefficient>0.95

(Step 150). Accordingly, the signal, whose computed parameters of the bell-shaped function are judged to be within the ranges assumed in a light signal corresponding to one light-emitting particle, as shown in FIG. 6 left, is judged as a signal corresponding to one light-emitting particle, and thereby one light-emitting particle has been detected. On the other hand, a pulse signal, whose computed parameters of the bell-shaped function are not within the assumed ranges, as shown in FIG. 6 right, is disregarded as noise. In this regard, together with the detection of signals of light-emitting particles, the counting of the number of signals, i.e., the counting of light-emitting particles, may be conducted.

The searching and judging of a pulse signal in the above-mentioned processes of steps 130-150 may be repetitively carried out throughout light intensity data (step 160). In this connection, the processes for detecting individually a signal from the light intensity data may be performed by an arbitrary way, other than the above-mentioned procedures.

(4) Process of Computing an Index Value Indicating a Translational Diffusional Characteristic of a Light-Emitting Particle (Step 170)

When the individual detection of signals of light-emitting particles as noted above has been done, an index value indicating a translational diffusional characteristic of each light-emitting particle is computed using the variation of the light intensity from each light-emitting particle during the circulating movement of the light detection region. For such an index value, there may be employed either of (i) the ratio between the intensity value of the signal of one light-emitting particle and the sum of the intensity values within the time regions separated by the time equal to the moving cycle time of the position of the light detection region before and after the signal of the one light-emitting particle (Hereafter, referred to as a "translational diffusion characteristic amount") and (ii) the diffusion constant of a light-emitting particle. Hereafter, the computation process of each index value is explained.

(i) Computation Process of a "Translational Diffusion Characteristic Amount"

As explained in conjunction with FIG. 3, since a light detection region is made to periodically circulate along a predetermined route, a light intensity value from the same spatial domain is measured every moving cycle time of the light detection region in the time series light intensity data. Consequently, the light intensity values in the time region previous by the time corresponding to the moving cycle time of the light detection region and in the time region subsequent by the time corresponding to the moving cycle time of the light detection region, measured from each of the generation times of the signals of the light-emitting particles detected till step 160, each reflect the conditions of the space in which the light emitting particle corresponding to each signal existed one cycle before and after, and those light intensity values are determined by the position of the light-emitting particle within the space. Thus, by comparing the light intensity value of a signal of a light-emitting particle with the respective light intensity values in the time regions previous and subsequent by the time corresponding to the moving cycle time of the light detection region measured from the generation time of said signal, it is possible to estimate the degree of the easiness of changing the position of the light-emitting particle in the moving cycle time of the light detection region, i.e., the degree of the easiness of the translational diffusion of the light emitting particle.

Then, in the present embodiment, for each of the signals of the light-emitting particles detected till step 160, there is employed, as an index value which shows the translational diffusional characteristic of each light-emitting particle, the ratio between the intensity value of the signal of each light-emitting particle and the sum of the intensity values within the time regions separated by the time equal to the moving cycle time of the position of the light detection region before and after the signal of the each light-emitting particle (Translational diffusion characteristic amount). Concretely, the translational diffusion characteristic amount may be defined with the photon count, pc, in the pulse existing region of the signal of one light-emitting particle; the photon count, $p_{-1}$, in the time region $\Delta Tf$ previous by the time corresponding to the moving cycle time of the position of the light detection region; and the photon count, $p_{+1}$, in the time region $\Delta Tr$ subsequent by the time corresponding to the moving cycle time of the position of the light detection region, as:

(Translational diffusion characteristic amount)=$(p_{-1}+p_{+1})/pc$      (6).

In this regard, the widths of the time regions $\Delta Tf$ and $\Delta Tr$ may be set arbitrarily experimentally or theoretically, and typically, may be the time taken for the light detection region to pass the distance equal to the maximum diameter of the light detection region. According to this translational diffusion characteristic amount, as schematically drawn in FIG. 7A, in a case of a comparatively large particle (left figure), since its moving speed by the Brownian motion is slow and its time to reside in the same spatial domain is long, the difference between the light intensity (photon count pc) of a signal and the light intensities (photon counts $p_{-1}$, $p_{+1}$) within the time regions before and after the generation time of the signal by the moving cycle time tcycle of the position of the light detection region is relatively small, and therefore, the translational diffusion characteristic amount defined by Expression (6) becomes large. On the other hand, in a case of a comparatively small particle (right figure), since its moving speed by the Brownian motion is quick and its time to reside in the same spatial domain is short, the difference between the light intensity (photon count pc) of a signal and the light intensities (photon counts $p_{-1}$, $p_{+1}$) within the time regions before and after the generation time of the signal by the moving cycle time tcycle of the position of the light detection region is relatively large or it is possible that the light-emitting particle is not present in the same space, and therefore the translational diffusion characteristic amount defined by Expression (6) becomes small. Thus, since the translational diffusion characteristic amount shows the translational diffusional characteristic of a light-emitting particle and is a value peculiar to the light-emitting particle, the translational diffusion characteristic amount can be used for discrimination or identification of a kind of light-emitting particle.

(ii) Computation Process of the Diffusion Constant of a Light-Emitting Particle

Referring to FIGS. 3A-3C again, if a light-emitting particle resides within a space encompassed when a light detection region CV exists in a certain position during the circulation of the light detection region as in FIG. 3A, the signals (pulse form signals) of the light-emitting particle appear almost every moving cycle time tcycle of the light detection region as illustrated by FIG. 3C. During this, as noted, the position of the light-emitting particle changes by the Brownian motion so that the light intensity in the series of the signals will vary. In this respect, this light intensity variation reflects the change of the position of the light-emitting particle in the radial direction from the maximum intensity point of the light detection region, and the light detection region is moving in one direction, and therefore, the variation in the peak intensities of the respective signals is considered to be caused by the translational diffusion motion of the light-emitting particle within a plane perpendicular to the moving direction of the light detection region as illustrated in FIG. 3B.

Supposing the translational diffusion motion of a light-emitting particle in a plane perpendicular to the moving direction of the light detection region follows the translational diffusion model by the two-dimensional Brownian motion, the autocorrelation function in time of the light intensity of the light-emitting particle of the diffusion constant D is given by:

[Expression 1]

$$G(\tau) = 1 + \frac{1}{N} \frac{1}{\left(1 + \frac{4D\tau}{W_o^2}\right)^{\frac{1}{2}} \left(1 + \frac{4D\tau}{W_z^2}\right)^{\frac{1}{2}}} \quad (7)$$

(Non-patent documents 5 and 6). Here, N is the average number of particles in the light detection region; $\tau$ is delay time; Wo is the minor axis diameter of the light detection region; and Wz is the major axis diameter of the light detection region (See FIG. 1B). In the case of the present invention, N=1 is established, and when AR=Wz/Wo, Expression (7) becomes:

[Expression 2]

$$G(\tau) = 1 + \frac{1}{1} \frac{1}{\left(1 + \frac{4D\tau}{W_o^2}\right)^{\frac{1}{2}} \left(1 + \frac{1}{AR^2}\frac{4D\tau}{W_o^2}\right)^{\frac{1}{2}}} \quad (8)$$

On the other hand, the autocorrelation function in time, computed from the light intensities of the signals of a light-emitting particle, is computed by:

[Expression 3]

$$G(\tau) = \frac{\langle 1(t)1(t+\tau)\rangle}{\langle 1(t)\rangle^2} \qquad (9)$$

Thus, in the present embodiment, first, a group of signals which appear every moving cycle time of a light detection region is extracted among the signals of light-emitting particle detected till step 160. In this extraction, one signal of a light-emitting particle is chosen in the time series light intensity data, and signals of light-emitting particle which exist in time regions separated from the generation time of the one signal by the time corresponding to an integral multiple of the moving cycle time of the position of the light detection region are selected as the signals of the same light-emitting particle, and then these are considered as the group of the signals of the one light-emitting particle. Furthermore, this operation may be conducted for the whole region of the time series light intensity data, and thus, a plurality of groups of signals of single light-emitting particles may be extracted in one time series light intensity data. Then, when a group of signals of a light-emitting particle is extracted, as shown in FIG. 7B, the autocorrelation function values of the light intensities of the group are computed with Expression (9), and then, the theoretical formula (the dotted line in the drawing), derived from the translational diffusion model explained above, is fit to the autocorrelation function values (the plotted points in the drawing), and thereby the diffusion constant D is computed. In the series of these processes, in the calculation of the autocorrelation function values of light intensity, with putting $\Delta t=t_{cycle}$, the autocorrelation function values may be computed in the group of the signals of a light-emitting particle according to Expression (9) for the respective cases of the group of signals in which the respective generation times are mutually separated by one cycle time ($\tau=\Delta t$); the group of signals in which the respective generation times are mutually separated by two cycle times ($\tau=2\Delta t$); the group of signals in which the respective generation times are mutually separated by three cycle times ($\tau=3\Delta t$); . . . (Thus, the number of terms in the numerator of Expression (9) is reduced with the length of $\tau$.) In addition, with respect to the theoretical formula derived from the translational diffusion model, in the case of the present embodiment, it is difficult to well acceptably carry out the fitting of Expression (7) or (8) because the number of points of the light intensity values for the computation of autocorrelation function values and the number of points of the computed autocorrelation function values are relatively small. Thus, in the present embodiment, preferably, only the 2nd term which characterizes the variation in the theoretical formula (8) may be fit to the autocorrelation function values. Namely, Expression obtained by modifying Expression (8) as described below may be used for the fitting expression.

[Expression 4]

$$G(\tau) = \frac{K}{\left(1+\frac{4D\tau}{W_o^2}\right)^{\frac{1}{2}}\left(1+\frac{1}{AR^2}\frac{4D\tau}{W_o^2}\right)^{\frac{1}{2}}} \qquad (10)$$

Here, K is a constant and is determined by the fitting. In this connection, in the fitting, instead of the diffusion constant D, for instance, a function value, etc. obtained by multiplying a constant on the diffusion constant may be computed, and it should be understood that such a case belongs to the scope of the present invention.

Thus, (i) the translational diffusion characteristic amount or (ii) the diffusion constant (or its function value) as mentioned above is determined for each light-emitting particle. As noted, since these values can be considered to be values peculiar to a light-emitting particle, discrimination or identification of the kind of light-emitting particle can be achieved for each light-emitting particle.

(5) Other Analyses

When the time series light intensity data is obtained in the above-mentioned processes, various analyses, such as light-emitting particle concentration calculation, may be further performed by processes according to programs memorized in storage apparatus in the computer 18.

For example, in the case that the number of light-emitting particles is determined by counting the number of signals of detected light-emitting particles, if the volume of the whole region through which the light detection region has passed is computed out by an arbitrary way, the number density or concentration of the light-emitting particle in the sample solution can be determined from the number of light-emitting particles and the volume. The volume of the whole region through which the light detection region has passed may be theoretically computed out with the wavelength of excitation light or detected light, the numerical aperture of lenses and the adjustment condition of the optical system, but the volume may be determined experimentally, for instance, using the number of light-emitting particles detected by performing, with a solution having a known light-emitting particle concentration (a reference solution), the light intensity measurement, detection of (a) light-emitting particle(s) and their counting under the same condition as the measurement of a sample solution to be tested, and the light-emitting particle concentration of the reference solution. Concretely, for example, supposing the number of detected light-emitting particles in N in a reference solution of the light-emitting particle concentration C, the whole volume Vt of the region through which the light detection region has passed is given by:

$$Vt=N/C \qquad (11).$$

Alternatively, by preparing the plurality of solutions of different light-emitting particle concentrations and performing the measurement for each of the solutions, the average value of the computed Vts may be employed as the whole volume Vt of the region through which the light detection region has passed. Then, when Vt is given, the concentration c of the light-emitting particle of the sample solution, whose counting result of the light-emitting particles is n, is given by:

$$c=n/Vt \qquad (12)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage device of the computer 18 the information on the relations (Expression (12)) between concentrations C and light-emitting particle numbers N of various standard light-emitting particles for assumed moving patterns of the light detection region, so that a user of the device can appropriately use the memorized information on the relation in conducting an optical analysis. It should be understood that, according to the present invention, since discrimination or identification of the kind is possible for each single light-emitting particle with the translational diffusion characteristic amount or diffusion constant, the concentration also can be determined for each (discriminable) kind of light-emitting particle.

In order to verify the validity of the present invention explained above, the experiments described below were conducted. In this regard, it should be understood that the following embodiments illustrate the validity of the present invention only, not intended to limit the scope of the present invention.

Embodiment 1

In the scanning molecule counting method, a translational diffusion characteristic amount defined by Expression (6) was computed for each of the signals of light-emitting particle detected in the time series light intensity data.

For sample solutions, there were prepared a solution containing a fluorescent dye TAMRA (M. W.430.45 Sigma-Aldrich Cat. No. C2734) as a light-emitting particle at 100 fM in a phosphate buffer (containing 0.05% Tween20) and a solution containing plasmid (pbr322, 2.9 MDa, Takara Bio, Inc. Cat. No. 3035) at 1 pM and DNA intercalator fluorescent dye SYTOX Orange (Invitrogen Corp. Cat. No. S-11368) at 10 nM in the phosphate buffer (SYTOX Orange binds with a single plasmid to be a single light-emitting particle.). In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) was acquired for the above-mentioned two sample solutions in accordance with the manner explained in the above-mentioned "(2) Measurement of Light Intensity of a Sample Solution". In that time, a 543-nm laser light was used for excitation light, and, using a band pass filter, the light of the wavelength band, 560 to 620 nm, was measured, generating time series photon count data. The moving speed of the position of the light detection region in the sample solution was set to 6000 rpm (15 mm/sec).; BIN TIME, 1 μsec., and the measurement was performed for 2 seconds.

In the data processing after the light measurement, first, for the acquired time series photon count data, in accordance with the way described in "(3) Individual Detection of a Signal of a Light-Emitting Particle" and steps 110-160 in FIG. 4, a smoothing treatment was applied to the time series photon count data, and after determining the start points and end points of pulse signals in the smoothed data, a Gauss function was fit to each pulse signal by the least-squares method, and the peak intensity, pulse width (full width at half maximum), and correlation coefficient (in the Gauss function) were determined. And only a pulse signal satisfying the following conditions was extracted as a signal corresponding to a light-emitting particle:

20 μseconds<pulse width<400 μseconds

Peak intensity>1[pc/10 μsec.]     (A)

Correlation coefficient>0.95.

Subsequently, the translational diffusion characteristic amount of Expression (6) was computed for each light-emitting particle signal. The time region $\Delta Tf$ previous by the time corresponding to the moving cycle time of the position of the light detection region was set to the section 10.05-9.95 m-seconds before the time point of the peak of a signal and the time region $\Delta Tr$ subsequent by the time corresponding to the moving cycle time of the position of the light detection region was set to the section 9.95-10.05 m-seconds after the time point of the peak of a signal.

FIG. 8A shows the average values (bar graphs) and standard deviations (error bars) of translational diffusion characteristic amounts of the fluorescent dye molecules, TAMRA, and the plasmids stained with the SYTOX Orange; and FIG. 8B shows the generation frequencies (histogram) of the translational diffusion characteristic amounts. With reference to the drawing, for the translational diffusion characteristic amounts, the average value (0.87) of the translational diffusion characteristic amounts of the large and slow-moving plasmids was a substantially larger value than the average value (0.18) of the translational diffusion characteristic amounts of the small and quick-moving fluorescent dye molecules TAMRA. Moreover, as clearly seen with reference to the histogram, there was only small overlap region in the histograms of the translational diffusion characteristic amounts of the plasmids and the translational diffusion characteristic amounts of the fluorescent dye molecules TAMRA. Actually, when, as a reference value, 0.6, obtained by subtracting 1 SD from the average value of the translational diffusion characteristic amounts of the plasmids was considered, the ratio of the signals of the fluorescent dye molecules TAMRA was 85% among the signals below the reference value (signals judged as a signal of the fluorescent dye molecule TAMRA), and the ratio of the signals of the plasmids was 89% among the signals beyond the reference values (signals judged as a signal of a plasmid). This result shows that discrimination of two kinds of light-emitting particles is substantially possible with the translational diffusion characteristic amount.

Embodiment 2

In the scanning molecule counting method, the diffusion constant was computed for each of the signals of light-emitting particle detected in the time series light intensity data through the processes described in "(ii) Computation Process of the Diffusion Constant of a Light-Emitting Particle".

For a sample solution, there was prepared a solution containing plasmids (pbr322, 2.9 MDa Takara Bio, Inc., Cat. No. 3035) at 1 pM and DNA intercalator fluorescent dye SYTOX Orange (Invitrogen Corp. Cat. No. S-11368) at 10 nM in a phosphate buffer (containing 0.05% Tween20). The light measurement and the individual detection of the light-emitting particle signals were performed similarly to Embodiment 1. However, a 633-nm laser light was used for the excitation light. After this, groups of signals of the same light-emitting particles are extracted among the detected light-emitting particle signals, and for each of the groups, the autocorrelation function values of Expression (9) were computed; the fitting of Expression (10) was carried to the computed autocorrelation function values; and the diffusion constant D and the minor axis diameter Wo of the light detection region were computed. In this respect, AR in Expression (10) was set to 3.5.

FIG. 9A shows examples of the peak intensities of the respective signals in signal groups, each specified as the signals of the same light-emitting particle, among the light-emitting particle signals detected in the time series light intensity data; and FIG. 9B shows the autocorrelation function values (plot point) of the peak intensities and fitting curves (dotted lines) for the signal groups, respectively. With reference to the drawings, Expression (10) was well acceptably fit to the autocorrelation function values. And, in the illustrated examples, the diffusion constant D and the minor axis diameter Wo of the light detection region, computed here, were as follows:

TABLE 1

| Particle | 1 | 2 | 3 | 4 | Average |
|---|---|---|---|---|---|
| D (×$10^{-12}$ m$^2$/sec) | 7.2 | 2.1 | 6.8 | 2.2 | 4.6 |
| W (μm) | 0.29 | 0.42 | 0.32 | 0.49 | 0.38 |

It is considered that the plasmid used for the measurements in a water solution has a molecular form between rod and spherical forms, and theoretically, the diffusion constant is estimated to be 4.2~22×$10^{-12}$ m$^2$/s, and therefore the above-mentioned results were in agreement with the theoretical estimate. In addition, since the radius (Wo) of the light detection region (confocal volume) is designed to be about 0.4 μm, and therefore, the above-mentioned result was almost in agreement with the design value. From these results, it has been shown that, in the scanning molecule counting method, it is possible to detect the signal of the same light-emitting particle multiple times and compute the diffusion constant of the light-emitting particle, and thereby there is acquired the information on a dynamic characteristic, i.e., the size (molecular weight, form) of a particle in a water solution to make it possible to identify a light-emitting particle.

Thus, as understood from the results of the above-mentioned embodiments, it has been shown that, in accordance with the teachings of the present invention, it is possible to determine individually for each light-emitting particle, an index value indicating a translational diffusional characteristic of the light-emitting particle in a plane perpendicular to the moving direction of a light detection region in the scanning molecule counting method, and such a index value can be used for discrimination or identification of the kind of light-emitting particle.

The invention claimed is:

1. An optical analysis device which detects light from a light-emitting particle dispersed and moving at random in a sample solution using an optical system of a confocal microscope or a multiphoton microscope, comprising:
a light detection region mover which periodically moves a position of a light detection region of the optical system along a predetermined route in the sample solution;
a light detector which detects a light amount from the light detection region; and
a signal processor which generates time series light intensity data of the light from the light detection region detected with the light detector during the moving of the position of the light detection region in the sample solution and detects a signal indicating light from a single light-emitting particle individually in the time series light intensity data;
wherein the signal processor determines an index value indicating a translational diffusional characteristic of the light-emitting particle in a plane perpendicular to a moving direction of the light detection region based upon an intensity value of a detected signal indicating light of one light-emitting particle and an intensity value within a time region separated from a generation time of the signal indicating light of the one light-emitting particle by a time corresponding to an integral multiple of a moving cycle of the position of the light detection region in the time series light intensity data.

2. The device of claim 1, determining a kind of the light-emitting particle with the index value indicating the translational diffusional characteristic of the light-emitting particle.

3. The device of claim 1, wherein the index value indicating the translational diffusional characteristic of the light-emitting particle is the ratio between an intensity value of a signal of one light-emitting particle and a sum of intensity values within time regions separated by a time corresponding to a moving cycle time of the position of the light detection region before and after the signal of the one light-emitting particle.

4. The device of claim 1, wherein the intensity value within the time region separated from the generation time of the signal indicating light of the one light-emitting particle by the time corresponding to the integral multiple of the moving cycle of the position of the light detection region in the time series light intensity data is an intensity value of a signal indicating light, generated in the time region, of the same light-emitting particle as the one light-emitting particle; and the index value indicating the translational diffusional characteristic of the light-emitting particle is a diffusion constant or its function value computed by fitting a theoretical formula derived from a translational diffusion model of the light-emitting particle in a plane perpendicular to the moving direction of the light detection region to autocorrelation function values in time computed with the intensity value of the signal indicating light of the one light-emitting particle and the intensity values of signals indicating light of the same light-emitting particle as the one light-emitting particle.

5. An optical analysis method of detecting light from a light-emitting particle dispersed and moving at random in a sample solution using an optical system of a confocal microscope or a multiphoton microscope, comprising steps of:
(a) moving a position of a light detection region of the optical system in the sample solution periodically along a predetermined route;
(b) measuring a light intensity from the light detection region during the moving of the position of the light detection in the sample solution to generate light intensity data;
(c) detecting individually a signal indicating light from a single light-emitting particle in the light intensity data; and
(d) determining an index value indicating a translational diffusional characteristic of one light-emitting particle in a plane perpendicular to a moving direction of the light detection region based upon an intensity value of a detected signal indicating light of the one light-emitting particle and an intensity value within a time region separated from a generation time of the signal indicating light of the one light-emitting particle by a time corresponding to an integral multiple of a moving cycle of the position of the light detection region in the time series light intensity data.

6. The method of claim 5, further comprising a step of (e) determining a kind of the light-emitting particle with the index value indicating the translational diffusional characteristic of the light-emitting particle.

7. The method of claim 5, wherein the index value indicating the translational diffusional characteristic of the light-emitting particle is the ratio between an intensity value of a signal of one light-emitting particle and a sum of intensity values within time regions separated by a time corresponding to a moving cycle time of the position of the light detection region before and after the signal of the one light-emitting particle.

8. The method of claim 5, wherein the intensity value within the time region separated from the generation time of the signal indicating light of the one light-emitting particle by the time corresponding to the integral multiple of the moving cycle of the position of the light detection region in the time series light intensity data is an intensity value of a signal indicating light, generated in the time region, of the same light-emitting particle as the one light-emitting particle; and the index value indicating the translational diffusional characteristic of the light-emitting particle is a diffusion constant or its function value computed by fitting a theoretical formula derived from a translational diffusion model of the light-emitting particle in a plane perpendicular to the moving direction of the light detection region to autocorrelation function values in time computed with the intensity value of the signal indicating light of the one light-emitting particle and the intensity values of signals indicating light of the same light-emitting particle as the one light-emitting particle.

9. A computer readable storage device having a computer program product including programmed instructions for optical analysis of detecting light from a light-emitting particle dispersed and moving at random in a sample solution using an optical system of a confocal microscope or a multiphoton microscope, said programmed instructions causing a computer to perform steps comprising:

moving a position of a light detection region of the optical system in the sample solution periodically along a predetermined route;

measuring a light intensity from the light detection region during the moving of the position of the light detection region in the sample solution to generate light intensity data;

detecting individually a signal indicating light from a single light-emitting particle in the light intensity data; and determining an index value indicating a translational diffusional characteristic of one light-emitting particle in a plane perpendicular to a moving direction of the light detection region based upon an intensity value of a detected signal indicating light of the one light-emitting particle and an intensity value within a time region separated from a generation time of the signal indicating light of the one light-emitting particle by a time corresponding to an integral multiple of a moving cycle of the position of the light detection region in the time series light intensity data.

10. The computer readable storage device of claim 9, further comprising a step of determining a kind of the light-emitting particle with the index value indicating the translational diffusional characteristic of the light-emitting particle.

11. The computer readable storage device of claim 9, wherein the index value indicating the translational diffusional characteristic of the light-emitting particle is the ratio between an intensity value of a signal of one light-emitting particle and a sum of intensity values within time regions separated by a time corresponding to a moving cycle time of the position of the light detection region before and after the signal of the one light-emitting particle.

12. The computer readable storage device of claim 9, wherein the intensity value within the time region separated from the generation time of the signal indicating light of the one light-emitting particle by the time corresponding to the integral multiple of the moving cycle of the position of the light detection region in the time series light intensity data is an intensity value of a signal indicating light, generated in the time region, of the same light-emitting particle as the one light-emitting particle; and the index value indicating the translational diffusional characteristic of the light-emitting particle is a diffusion constant or its function value computed by fitting a theoretical formula derived from a translational diffusion model of the light-emitting particle in a plane perpendicular to the moving direction of the light detection region to autocorrelation function values in time computed with the intensity value of the signal indicating light of the one light-emitting particle and the intensity values of signals indicating light of the same light-emitting particle as the one light-emitting particle.

* * * * *